United States Patent
Hong et al.

(10) Patent No.: US 10,948,556 B2
(45) Date of Patent: Mar. 16, 2021

(54) METHOD FOR MODIFYING AND CONTROLLING MAGNETIC FIELD AND APPARATUS FOR THE SAME

(71) Applicant: Electronics and Telecommunications Research Institute, Daejeon (KR)

(72) Inventors: Hyo-Bong Hong, Daejeon (KR); Jae-Chan Jeong, Daejeon (KR); Seung-Min Choi, Daejeon (KR); Chang-Beom Kim, Seoul (KR)

(73) Assignee: Electronics and Telecommunications Research Institute, Daejeon (KR)

(*) Notice: Subject to any disclaimer, the term of this patent is extended or adjusted under 35 U.S.C. 154(b) by 197 days.

(21) Appl. No.: 16/205,044

(22) Filed: Nov. 29, 2018

(65) Prior Publication Data
US 2019/0162801 A1    May 30, 2019

(30) Foreign Application Priority Data

Nov. 30, 2017  (KR) .......... 10-2017-0162955
Nov. 30, 2017  (KR) .......... 10-2017-0162961

(51) Int. Cl.
*G01R 33/36* (2006.01)
*G01R 33/48* (2006.01)
(Continued)

(52) U.S. Cl.
CPC .......... *G01R 33/36* (2013.01); *G01R 33/381* (2013.01); *G01R 33/48* (2013.01); *A61N 2/00* (2013.01);
(Continued)

(58) Field of Classification Search
USPC ........................ 361/143, 146, 148
See application file for complete search history.

(56) References Cited

U.S. PATENT DOCUMENTS 7,675,288 B2    3/2010  Lee et al.
2009/0131736 A1*  5/2009  Jonckheere .......... A61B 5/4893
                                              600/12
(Continued)

FOREIGN PATENT DOCUMENTS

JP      3513597 B2     3/2004
KR    1020050064196 A   6/2005
(Continued)

OTHER PUBLICATIONS

Bernhard Gleich et al., "Tomographic imaging using the nonlinear response of magnetic particles," Nature international journal of science, Jun. 30, 2005, pp. 1214-1217, vol. 435.

*Primary Examiner* — Danny Nguyen
(74) *Attorney, Agent, or Firm* — William Park & Associates Ltd.

(57) ABSTRACT

Disclosed herein are a method for modifying a magnetic field using magnetic nanoparticles and an apparatus therefor. The method for modifying a magnetic field includes applying current to a single solenoid coil or to two parallel solenoid coils, measuring a strength of a magnetic field generated by the current at a preset target location using a measurement sensor, and controlling the strength of the magnetic field based on a concentration of a magnetic nanoparticle sample mounted in the single solenoid coil or the two solenoid coils so that the strength of the magnetic field matches a preset target value.

14 Claims, 15 Drawing Sheets

(51) Int. Cl.
  *G01R 33/381* (2006.01)
  *G01N 27/72* (2006.01)
  *A61N 2/00* (2006.01)
  *H05G 1/60* (2006.01)
  *G01R 33/12* (2006.01)

(52) U.S. Cl.
  CPC .............. *G01N 27/72* (2013.01); *G01R 33/12* (2013.01); *H05G 1/60* (2013.01)

(56) References Cited

U.S. PATENT DOCUMENTS

2013/0226516 A1   8/2013   Jeon et al.
2014/0306698 A1*  10/2014  Bontus ................... G01R 33/02
                                                        324/234

FOREIGN PATENT DOCUMENTS

| KR | 1020110071871 A | 6/2011 |
| KR | 101256500 B1 | 4/2013 |
| KR | 101393542 B1 | 5/2014 |

* cited by examiner

METHOD FOR MODIFYING AND CONTROLLING MAGNETIC FIELD AND APPARATUS FOR THE SAME

CROSS REFERENCE TO RELATED APPLICATIONS

This application claims the benefit of Korean Patent Application Nos. 10-2017-0162955, filed Nov. 30, 2017 and 10-2017-0162961, filed Nov. 30, 2017, which are hereby incorporated by reference in their entirety into this application.

BACKGROUND OF THE INVENTION

1. Technical Field

The present invention relates generally to technology for changing or controlling the strength of a magnetic field, and more particularly, to technology that can control the strength of a magnetic field using only magnetic nanoparticles without using a multi-coil array, and can also control the strength of a magnetic field so that the magnetic field is usable in fields such as electromagnetics, electric wave engineering, and the development of medical monitoring equipment by adjusting individual currents to be applied to multiple drive coils.

2. Description of the Related Art

One of the most essential parts in equipment for acquiring signals or images using electromagnetic fields in modern society, for example, medical imaging equipment or analytic chemistry equipment, is a solenoid coil. Such a solenoid coil is used as an inductor in electronic parts, but is used as a Helmholtz coil (or a Maxwell coil) for applying an electromagnetic field or acquiring a signal in medical imaging equipment. Further, solenoid coils are used in various forms, such as a circular form, which is the most common type, an elliptical form, a rectangular form, or a saddle-coil form in which a coil is curved along a curved surface, depending on the shapes of the solenoid coils.

In this case, with the exception of a solenoid coil used as an inductor, the primary purpose of various solenoid coils is to form a specific magnetic field in a two-dimensional (2D) or three-dimensional (3D) space. Most solenoid coils are developed to aim to form a magnetic field so that the magnetic field is uniformly distributed in a 2D or 3D space. For example, Magnetic Resonance Imaging (MRI) machines, widely used in hospitals, require a coil for forming a 1.5 T (Tesla) magnetic field over the entire region to be imaged.

Further, after a constant magnetic field has been formed in a specific space, a magnetic field strength required for acquisition of images may be secured by mounting additional coils on different axes and moving a magnetic field in 2D or 3D. This technology is expressed as the formation of a gradient field in MRI or Electron Paramagnetic Resonance Imaging (EPRI). Also, in Magnetic Particle Imaging (MPI), such technology is expressed as the shift of a Field-Free Line (FFL) or Field-Free Point (FFP) or as the formation of an electromagnetic magnetic probe.

That is, although this technology is applied to different fields, the basic configuration for always forming a magnetic field on a main axis and changing the magnetic field formed on the main axis using coils on other axes is identical in the fields. However, this configuration is problematic in that many coils must be used and in that a power supply, a controller required for current control, etc. are additionally required in order to supply electricity to the many coils.

Further, once a coil having such a structure is manufactured, it is realistically almost impossible to modify the coil structure, and thus an operational problem arises in that expensive coils must be discarded or manufactured again. Furthermore, when a magnetic field having a specific strength is intended to be formed in a specific portion of a sample, there is inconvenience in that at least four voltages/currents must be adjusted in a 2D space and at least six voltages/currents must be adjusted in a 3D space, and the adjusted currents/voltages must be actually measured and then used. In order to overcome this inconvenience, a system function for a coil must be generated, and a lot of time is taken to reach a desired solution.

Also, the development of imaging equipment using an electromagnetic field in modern society has been recognized as very important technology in all industrial and academic fields, without being limited to medical fields. The fundamental principles of imaging equipment using electromagnetic fields are to use a resonance phenomenon between a magnetic field using the Larmor frequency and an applied Radio Frequency (RF) signal. Such a Larmor frequency may be the resonant frequency of an electron or nucleus which performs precession in the magnetic field, and may also be important information by which the location at which a resonance phenomenon occurs can be determined when a magnetic field is a gradient field.

Here, the Larmor frequency may be represented by the following Equation (1):

$$\omega = \gamma_{N or E} B_0 \quad (1)$$

In Equation (1), ω (Omega) denotes the Larmor frequency, γ (Gamma) denotes a gyroscopic ratio, N denotes a nucleolus. E denotes an electron, and B denotes an external magnetic field. As shown in Equation (1), gamma is a constant regardless of whether the resonance is electron resonance or nuclear resonance. Since the strengths of magnetic fields for respective locations are known in a system to which the gradient field is applied, the location of a plane may be very easily calculated.

Based on these principles, a current Magnetic Resonance Imaging (MRI) system and an Electron Spin Resonance Imaging (ESRI) system are each generally composed of three parts, that is, a coil system which generates a fixed gradient field, an RF control system which applies a high frequency, and a system which controls equipment and processes signals. Therefore, in order to acquire images of a specific sample, there is required a process for applying a gradient field to a target sample on three axes, and thereafter applying a continuous RF field or pulse.

However, in order to measure only a specific portion of a sample using technology developed to date, a sample itself, which is a measurement target, must be reduced, or alternatively, a special adaptor must be used. For example, in the case of MRI, data about only a specific portion may be obtained only when a resonator must be separately designed and used. Also, there is technical inconvenience in that, in order to obtain a 3D resonance signal related to the specific portion, the entire portion corresponding to the periphery of the specific portion must be imaged, after which information about the specific portion must be acquired based on imaged results. In connection with this, Korean Patent Application Publication No. 10-2011-0071871 discloses a technology related to "Method and apparatus for size classification of metallic nanoparticles by using pulsed magnetic fields".

SUMMARY OF THE INVENTION

Accordingly, the present invention has been made keeping in mind the above problems occurring in the prior art, and an object of the present invention is to modify the strength of a magnetic field using magnetic nanoparticles without using a multi-coil system.

Another object of the present invention is to minimize the use of equipment that is required in order to modify the strength of a magnetic field.

A further object of the present invention is to provide a method for modifying a magnetic field, which is more easily used and is more efficiently implemented from the standpoint of expense than a method using multiple coils.

Yet another object of the present invention is to provide a method that is capable of generating an electromagnetic field in a specific space in a Nuclear Magnetic Resonance (NMR) system or an Electron Paramagnetic Resonance Imaging (EPRI) system that acquires an image using a fixed gradient field.

Still another object of the present invention is to provide technology that is capable of generating a magnetic field having a strength desired by a user at a desired location, thus enabling the magnetic field to be applied to a system using electron resonance or nuclear resonance.

Still another object of the present invention is to selectively apply an electromagnetic field for producing resonance to a specific location in space.

Still another object of the present invention is to provide an image acquisition scheme that is active rather than being passive as in the case where a gradient field is used.

In accordance with an aspect of the present invention to accomplish the above objects, there is provided a method for modifying a magnetic field, including applying current to a single solenoid coil or to two parallel solenoid coils; measuring a strength of a magnetic field generated by the current at a preset target location using a measurement sensor; and controlling the strength of the magnetic field based on a concentration of a magnetic nanoparticle sample mounted in the single solenoid coil or the two solenoid coils so that the strength of the magnetic field matches a preset target value.

The magnetic nanoparticle sample may be mounted in a cylinder corresponding to the single solenoid coil or the two solenoid coils.

Controlling the strength of the magnetic field may be performed using multiple magnetic nanoparticle samples, wherein the magnetic nanoparticle samples have different concentrations of magnetic nanoparticles.

Applying the current may be configured to, when the preset target location is in a two-dimensional (2D) space, apply the current to the single solenoid coil, and when the preset target location is in a three-dimensional (3D) space, apply the current to the two solenoid coils.

The two solenoid coils may have a shape corresponding to any one of a Helmholtz coil and a Maxwell coil.

The magnetic nanoparticle sample may be mounted in one or more of the two solenoid coils when the magnetic nanoparticle sample is intended to be mounted in the two solenoid coils.

In accordance with another aspect of the present invention to accomplish the above objects, there is provided an apparatus for modifying a magnetic field, including a power supply unit for applying current to a single solenoid coil or to two parallel solenoid coils; and a control unit for measuring a strength of a magnetic field generated by the current at a preset target location using a measurement sensor and controlling the strength of the magnetic field based on a concentration of a magnetic nanoparticle sample mounted in the single solenoid coil or the two solenoid coils so that the strength of the magnetic field matches a preset target value.

The magnetic nanoparticle sample may be mounted in a cylinder corresponding to the single solenoid coil or the two solenoid coils.

The control unit may be capable of using multiple magnetic nanoparticle samples, and the multiple magnetic nanoparticle samples may have different concentrations of magnetic nanoparticles.

The power supply unit may be configured to, when the preset target location is in a two-dimensional (2D) space, apply the current to the single solenoid coil, and when the preset target location is in a three-dimensional (3D) space, apply the current to the two solenoid coils.

The two solenoid coils may have a shape corresponding to any one of a Helmholtz coil and a Maxwell coil.

The magnetic nanoparticle sample may be mounted in one or more of the two solenoid coils when the magnetic nanoparticle sample is intended to be mounted in the two solenoid coils.

In accordance with a further aspect of the present invention to accomplish the above objects, there is provided a method for controlling a magnetic field, including applying current to one or more of a single solenoid coil for generating a magnetic field in a direction of a Z axis and multiple drive coils provided at preset intervals on a circumference of a concentric circle around one point on the Z axis; measuring a strength of a magnetic field at a target location at which the magnetic field is to be generated, using a measurement sensor that is movable on an X axis and a Y axis; and controlling the strength of the magnetic field by adjusting current to be applied to the multiple drive coils so that the strength of the magnetic field matches a preset target value.

Applying the current may be configured to apply individual currents to the multiple drive coils using a relay and variable resistors.

Controlling the strength of the magnetic field may be configured to adjust the individual currents by controlling respective variable resistors for the multiple drive coils.

The single solenoid coil and the concentric circle may be located parallel to each other.

Controlling the strength may be configured to control the strength of the magnetic field by changing locations of poles corresponding to the single solenoid coil.

Applying the current may be configured to apply the individual currents by controlling the relay based on an Arduino board.

In accordance with yet another aspect of the present invention to accomplish the above objects, there is provided an apparatus for controlling a magnetic field, including a power supply unit for applying current to one or more of a single solenoid coil for generating a magnetic field in a direction of a Z axis and multiple drive coils provided at preset intervals on a circumference of a concentric circle around one point on the Z axis; and a control unit for measuring a strength of a magnetic field at a target location at which the magnetic field is to be generated using a measurement sensor that is movable on an X axis and a Y axis and for controlling the strength of the magnetic field by adjusting current to be applied to the multiple drive coils so that the strength of the magnetic field matches a preset target value.

The power supply unit may apply individual currents to the multiple drive coils using a relay and variable resistors.

The control unit may adjust the individual currents by controlling respective variable resistors for the multiple drive coils.

The single solenoid coil and the concentric circle may be located parallel to each other.

The control unit may control the strength of the magnetic field by changing locations of poles corresponding to the single solenoid coil.

The power supply unit may apply the individual currents by controlling the relay based on an Arduino board.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
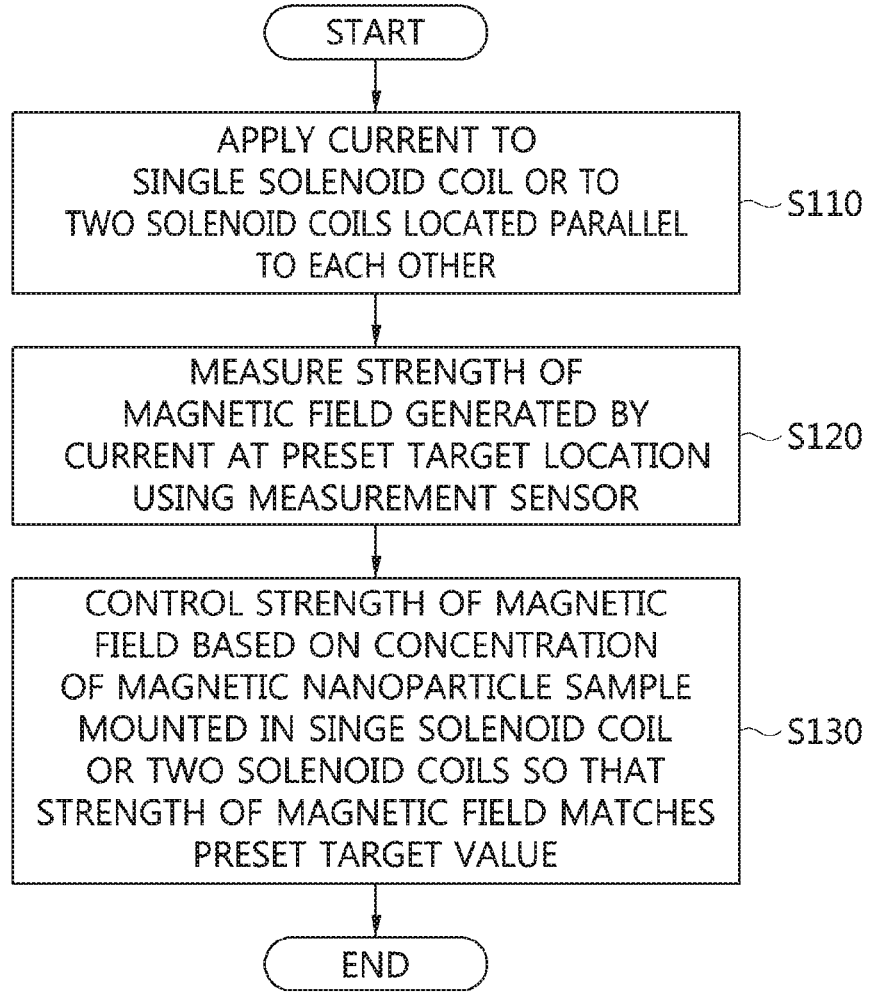
FIG. 1 is an operation flowchart illustrating a method for modifying a magnetic field according to an embodiment of the present invention.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, preferred embodiments of the present invention will be described in detail with reference to the attached drawings.

FIG. 1 is an operation flowchart illustrating a method for modifying a magnetic field according to an embodiment of the present invention.

Referring to FIG. 1, in the magnetic field modification method according to the embodiment of the present invention, current is applied to a single solenoid coil or to two parallel solenoid coils at step S110.

The single solenoid coil or each of the two solenoid coils may be a coil in which a conducting wire made of copper or aluminum is spirally and uniformly wound and formed in a cylindrical shape. Therefore, when current is applied to the conducting wire, a magnetic field having a relatively uniform strength may be formed in the direction penetrating into the cylindrical shape.

Here, the two solenoid coils may have a shape corresponding to any one of a Helmholtz coil and a Maxwell coil.

The Helmholtz coil may be composed of two identical solenoid coils, and may be configured such that the two solenoid coils are arranged parallel to each other while sharing a central axis with each other, with an area for magnetic field measurement being interposed therebetween.

The Maxwell coil has evolved from the Helmholtz coil and generates a magnetic field that is much more uniform than that of the Helmholtz coil, but requires more complicated settings than that of the Helmholtz coil.

Here, the current may be supplied through a power supply.

When a preset target location is in a 2D space, current may be applied to the single solenoid coil, and when the preset target location is in a 3D space, current may be applied to the two solenoid coils. That is, when a user desires to generate a magnetic field having a desired strength in a 2D space, the magnetic field may be generated by applying current only to one solenoid coil, and when the user desires to generate a magnetic field having a desired strength in a 3D space, the magnetic field may be generated by applying current to the two solenoid coils.

A structure for generating a magnetic field in a 2D space and a structure for generating a magnetic field in a 3D space will be described in detail later with reference to FIGS. 2 and 3.

Next, in the magnetic field modification method according to the embodiment of the present invention, the strength of a magnetic field generated by the current at the preset target location is measured using a measurement sensor at step S120.

Here, the target location may be the location where the strength of the magnetic field is to be subsequently modified through a magnetic nanoparticle sample. Therefore, at the target location, a sample-mounting hole in which the magnetic nanoparticle sample is to be mounted may be present.

Therefore, the strength of the magnetic field may be measured based on the central point of the sample-mounting hole in which the magnetic nanoparticle sample is not yet mounted.

The sample-mounting hole is included in an acrylic structure to fix the magnetic nanoparticle sample, and the structure of the sample-mounting hole will be described in detail later with reference to FIG. 4.

Here, the measurement sensor may measure the strength of a magnetic field while moving on an X axis and a Y axis in the area of an internal concentric circle in which the magnetic field is generated through the solenoid coil. Therefore, the measurement sensor may be moved while being fixed on an XY stage, on which the measurement sensor can be moved on the X axis and the Y axis.

The detailed structures of the measurement sensor and the XY stage will be described in detail later with reference to FIGS. 2 and 3.

Next, in the magnetic field modification method according to the embodiment of the present invention, the strength of the magnetic field is controlled based on the concentration of the magnetic nanoparticle sample mounted in the singe solenoid coil or two solenoid coils so that the strength of the magnetic field matches the preset target value at step S130.

For example, when magnetic nanoparticles are present at the location at which the magnetic field is formed, a change in the magnetic field may occur due to the magnetic force of the magnetic nanoparticles. Therefore, the strength of the magnetic field may be controlled by adjusting such a change using the concentration of the magnetic nanoparticles.

The magnetic nanoparticle sample may be mounted in a cylinder corresponding to the single solenoid coil or two solenoid coils.

For example, a container filled with a solution containing the magnetic nanoparticles may be fitted into the sample-mounting hole, and may then be mounted in the cylinder corresponding to the solenoid coil.

Here, multiple magnetic nanoparticle samples may be used, and may have different concentrations of magnetic nanoparticles.

For example, a first sample, in which the concentration of magnetic nanoparticles is 100%, a second sample, in which the concentration of magnetic nanoparticles is 50%, and a third sample, in which the concentration of magnetic nanoparticles is 25%, may be simultaneously mounted in a single solenoid coil.

Here, the method for mounting a magnetic nanoparticle sample in the sample-mounting hole will be described in detail later with reference to FIGS. 5 and 6.

When magnetic nanoparticle samples are intended to be mounted in two solenoid coils, the magnetic nanoparticle samples may be mounted in one or more of the two solenoid coils. That is, the magnetic nanoparticle samples may be mounted in only one of the two solenoid coils or may be mounted in the two solenoid coils, thus modifying a magnetic field.

By means of this magnetic field modification method, the modification of a magnetic field may be partially induced in a solenoid coil-type electromagnetic field generation device.

Also, there can be provided a magnetic field modification method, which can minimize the use of equipment required for the modification of the strength of a magnetic field and which can be more easily used and can be more efficiently implemented from the standpoint of expense than other methods using multiple coils.

Figure 2:
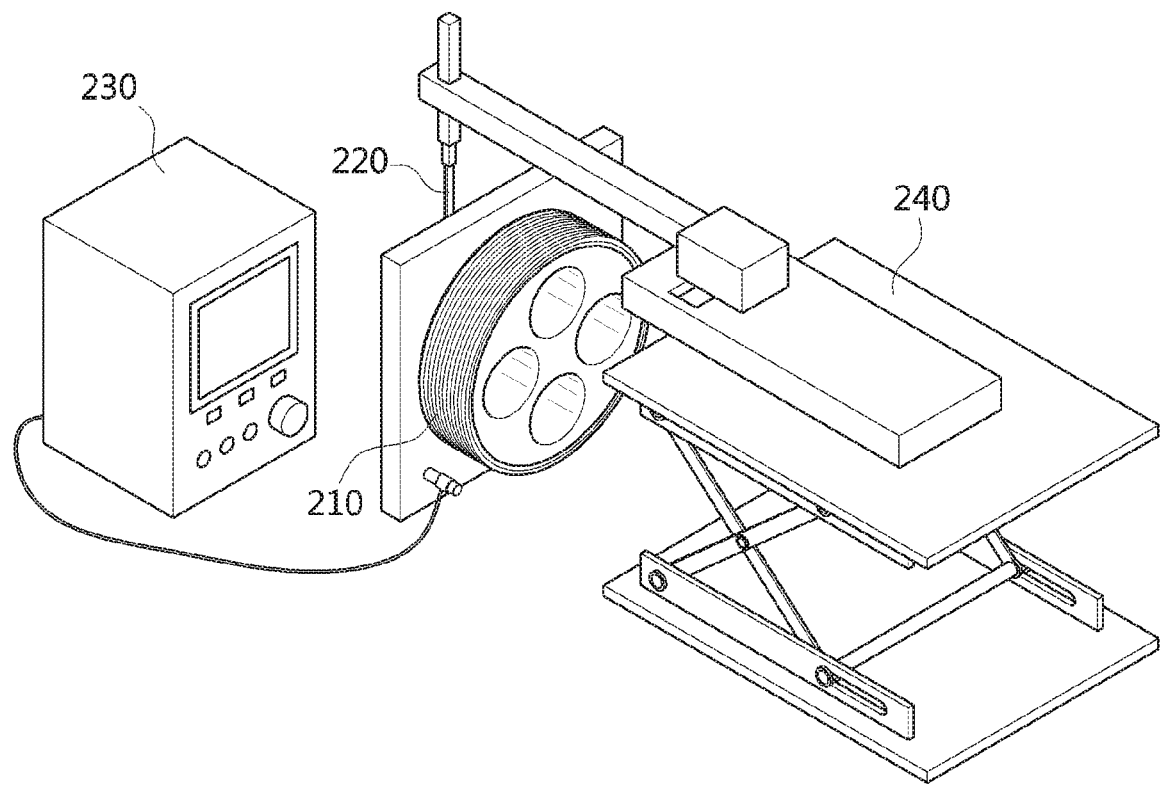
FIG. 2 is a view illustrating an example of a 2D magnetic field modification system according to the present invention.

FIG. 2 is a view illustrating an example of a 2D magnetic field modification system according to the present invention.

Referring to FIG. 2, the 2D magnetic field modification system according to the present invention includes a single solenoid coil 210, a measurement sensor 220, a power supply 230, and an XY stage 240.

Here, the single solenoid coil 210 may be generated by winding an enamel-coated copper wire several times. For example, the solenoid coil 210 used in the present embodiment may be generated by winding the enamel-coated copper wire 110 times to have a diameter of 114 mm.

A separate acrylic structure for mounting a magnetic nanoparticle sample may be provided in the cylinder of the solenoid coil 210.

Figure 4:
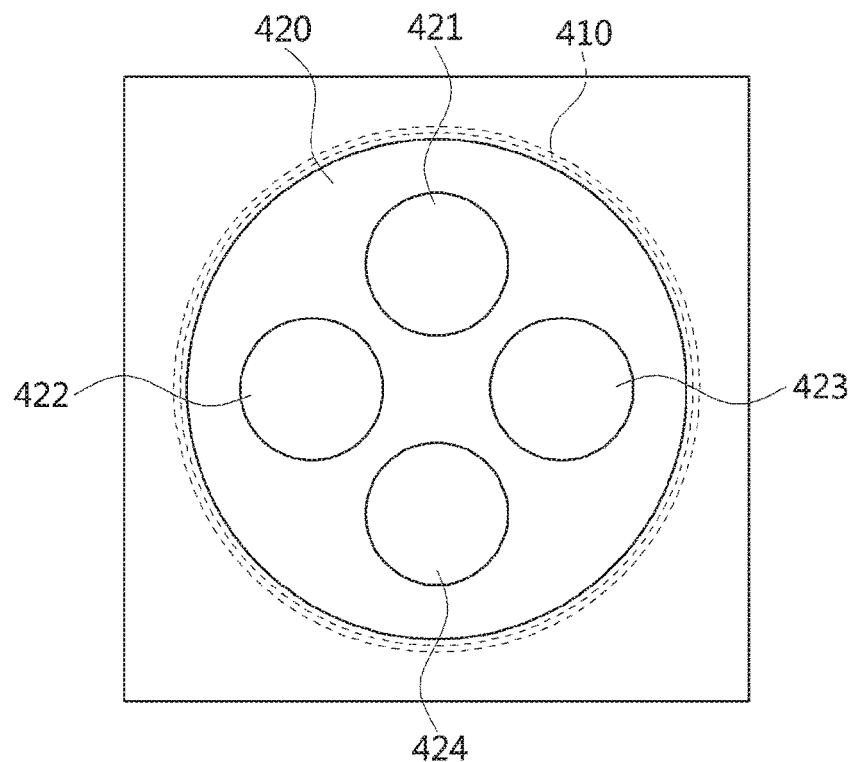
FIG. 4 is a view illustrating an example of an acrylic structure for mounting a magnetic nanoparticle sample in a solenoid coil according to the present invention.

For example, referring to FIG. 4, an acrylic structure 420 including multiple sample-mounting holes 421 to 424 for mounting magnetic nanoparticle samples may be provided in the cylinder of a solenoid coil 410 according to an embodiment of the present invention.

Here, the acrylic structure 420 may be replaced with a structure having different types of sample-mounting holes depending on the shape of the magnetic nanoparticle sample to be mounted.

Here, each of the sample-mounting holes 421 to 424 may be formed at the location desired by a user, and may have a shape corresponding to that of a container holding the corresponding magnetic nanoparticle sample.

Further, the measurement sensor 220 illustrated in FIG. 2 may be connected to the XY stage 240, and may measure a magnetic field while moving on an X axis and a Y axis. For example, the measurement sensor 220 used in the embodiment of the present invention may be a Hall sensor, and may be an F. W. Bell 5100 series or a Lutron MG-3002 series.

Next, the magnetic field modification system according to the present invention may apply current to the single solenoid coil 210 through the power supply 230.

That is, when the power supply 230 applies current to the single solenoid coil 210, the solenoid coil 210 may generate a magnetic field in a 2D space, and the measurement sensor 220 may measure the strength of the generated magnetic field and provide the measured strength to the user via a separate display. Thereafter, when the user desires to partially change the strength of the magnetic field, the strength of the magnetic field may be modified by mounting the magnetic nanoparticle sample at the location at which the strength of the magnetic field is desired to be changed.

Here, the strength of the magnetic field may be finely controlled by adjusting the concentration of the magnetic nanoparticle sample to be mounted.

Figure 3:
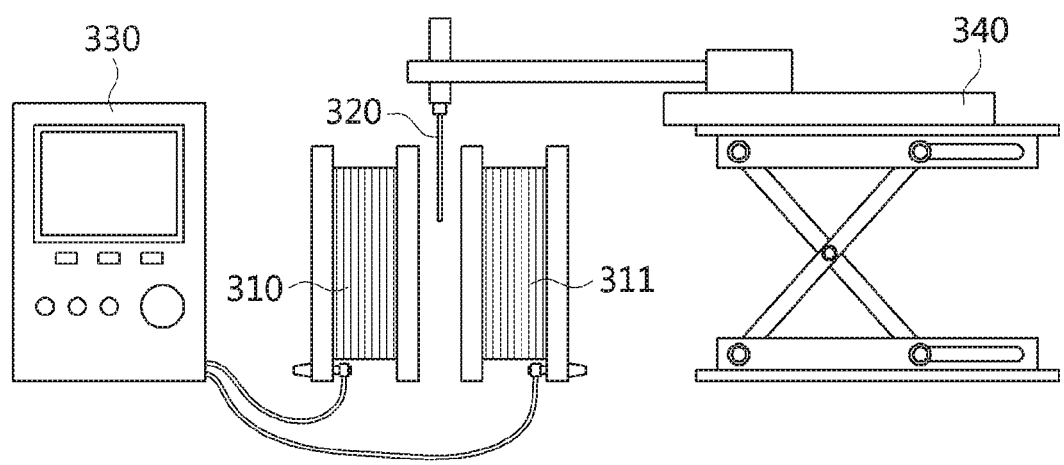
FIG. 3 is a view illustrating an example of a 3D magnetic field modification system according to the present invention.

FIG. 3 is a view illustrating an example of a 3D magnetic field modification system according to the present invention.

Referring to FIG. 3, the 3D magnetic field modification system according to the present invention includes two solenoid coils 310 and 311, a measurement sensor 320, a power supply 330, and an XY stage 340.

It can be seen that, when the system of FIG. 3 is compared with that of FIG. 2, one solenoid coil 210 is used in FIG. 2, whereas two solenoid coils 310 and 311 are used in FIG. 3.

Here, the two solenoid coils 310 and 311 may have the shape of a Helmholtz coil or a Maxwell coil by adjusting the directions of currents respectively applied to the two solenoid coils 310 and 311.

For example, when the directions of currents applied to the two solenoid coils 310 and 311 are identical to each other, a magnetic field may be generated in the shape of the Helmholtz coil, in which different polarities meet at the location of the measurement sensor 320.

In another example, when the directions of currents applied to the two solenoid coils 310 and 311 are different from each other, a magnetic field may be generated in the shape of the Maxwell coil, in which identical polarities meet at the location of the measurement sensor 320.

Here, as illustrated in FIG. 3, the present invention may apply respective currents to the two solenoid coils 310 and 311 through the power supply 330. That is, when the currents are applied to the two solenoid coils 310 and 311 through the power supply 330, a magnetic field corresponding to a 3D shape may be formed at the location at which the measurement sensor 320 is placed.

Also, the measurement sensor 320 may be connected to the XY stage 340, and may measure a magnetic field while freely moving on the X axis and the Y axis.

When the user desires to partially change the strength of the magnetic field, the strength of the magnetic field may be modified by mounting a magnetic nanoparticle sample at the location at which the strength of the magnetic field is desired to be changed.

A magnetic nanoparticle sample may be mounted in only one of the two solenoid coils 310 and 311, or alternatively, magnetic nanoparticle samples may be mounted in both of the two solenoid coils.

For example, it may be assumed that the two solenoid coils 310 and 311 have the shape of the Helmholtz coil and that currents are applied to cause both the solenoid coils 310 and 311 to generate a magnetic force of 30 Gauss. In this case, when magnetic nanoparticle samples of an undiluted solution concentration, containing magnetic nanoparticles of 25 g, are mounted in the two solenoid coils 310 and 311, the strength of a magnetic field at the center where the samples are mounted may be 45 Gauss. However, when the two solenoid coils 310 and 311 have the shape of the Maxwell coil, the strength of a magnetic field may be decreased below 10 Gauss.

In another example, it may be assumed that, as described above, the two solenoid coils 310 and 311 have the shape of the Helmholtz coil and that currents are applied to cause the two solenoid coils 310 and 311 to generate a magnetic force of 30 Gauss. In this case, when a magnetic nanoparticle sample of an undiluted solution concentration, containing magnetic nanoparticles of 25 g, is mounted in only one of the two solenoid coils 310 and 311, the strength of a magnetic field at the center at which the sample is mounted may be 35 Gauss. However, when the two solenoid coils 310 and 311 have the shape of the Maxwell coil, the strength of a magnetic field may have such a small value that the strength cannot be measured (less than or equal to 5 Gauss).

Figure 5:
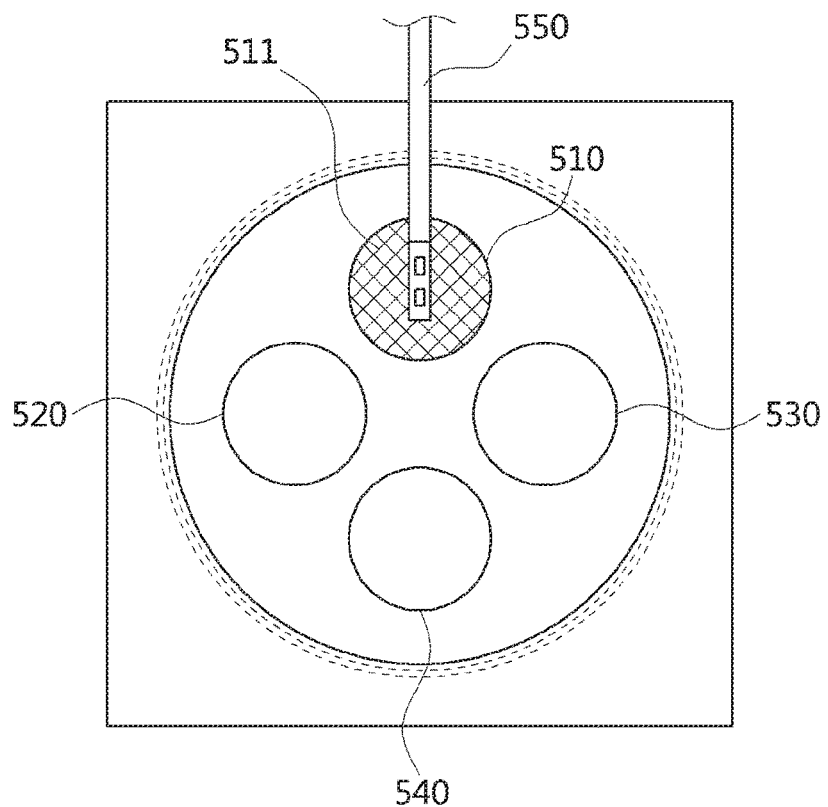
FIG. 5 is a view illustrating an example in which a magnetic nanoparticle sample is mounted in an acrylic structure according to the present invention.

FIG. 5 is a view illustrating an example in which a magnetic nanoparticle sample is mounted in an acrylic structure according to the present invention.

Referring to FIG. 5, a magnetic nanoparticle sample 511 according to the present invention may be detachably mounted in the sample-mounting hole 510 of an acrylic structure provided in a solenoid coil.

The magnetic nanoparticle sample 511 may be a sample generated by mixing magnetic nanoparticles with a solution and putting the resulting solution in a container made of a plastic material or the like. Therefore, samples having various concentrations may be acquired by adjusting the amount of magnetic nanoparticles mixed with the solution.

As illustrated in FIG. 5, the strength of a modified magnetic field may be measured by a measurement sensor 550 at the central location of the magnetic nanoparticle sample 511.

For example, it may be assumed that, before the magnetic nanoparticle sample 511 is mounted, the strength of a magnetic field measured at the center of the sample-mounting hole 510 is 20 Gauss when a voltage of 1.54 V and a current of 1.5 A are applied to the solenoid coil based on a resistor of 1.136 Ohm. Even if the strength of a magnetic field is measured based on the central point of each of the remaining sample-mounting holes 520, 530, and 540, it may be assumed that a strength falling within a range of about 18+/−1 Gauss is measured. When a magnetic nanoparticle sample 511 of an undiluted solution concentration, containing magnetic nanoparticles of 25 g, is mounted in the sample-mounting hole 510, and the strength of the magnetic field is again measured, a magnetic field having a strength of about 28 Gauss to 30 Gauss may be detected at the central point of each of the sample-mounting holes 510, 520, 530, and 540.

Figure 6:
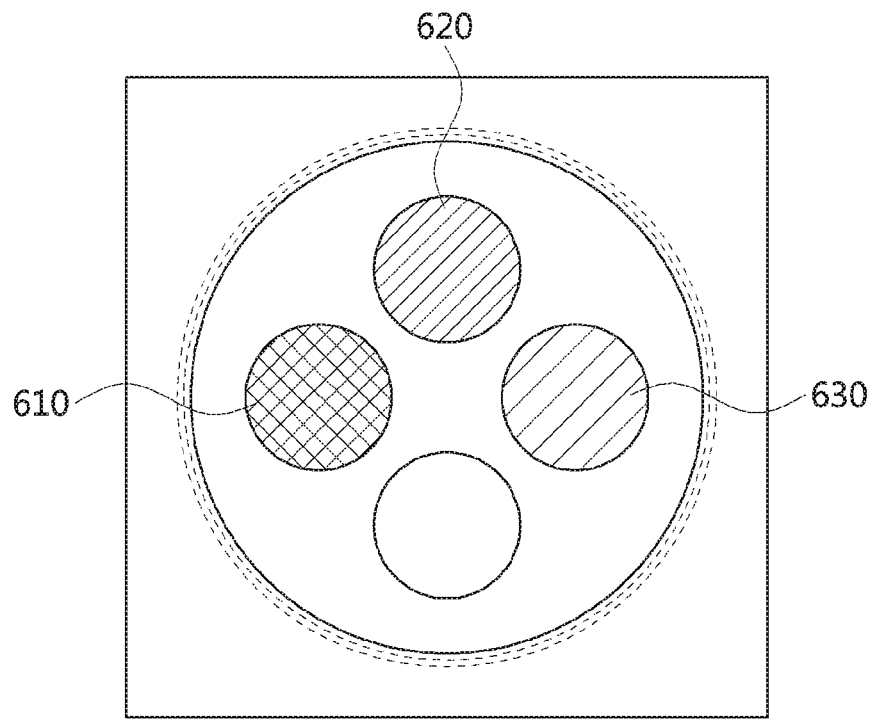
FIG. 6 is a view illustrating an example in which multiple magnetic nanoparticle samples are mounted in an acrylic structure according to the present invention.

FIG. 6 is a view illustrating an example in which multiple magnetic nanoparticle samples are mounted in an acrylic structure according to the present invention.

Referring to FIG. 6, multiple magnetic nanoparticle samples 610, 620, and 630 according to the present invention may be simultaneously mounted in a single solenoid coil.

Here, the concentrations of the magnetic nanoparticle samples 610, 620, and 630 may be different from each other.

For example, assuming that the magnetic nanoparticle sample 610 is an undiluted solution having a concentration of 100%, the concentration of the magnetic nanoparticle sample 620 may be 50%, and the concentration of the magnetic nanoparticle sample 630 may be 25%.

Here, since the influence on a magnetic field may differ depending on the concentrations of the magnetic nanoparticles, the strength of the magnetic field may be freely controlled merely by differently setting the concentration of the magnetic nanoparticles without requiring an additional coil or changing current.

Figure 7:
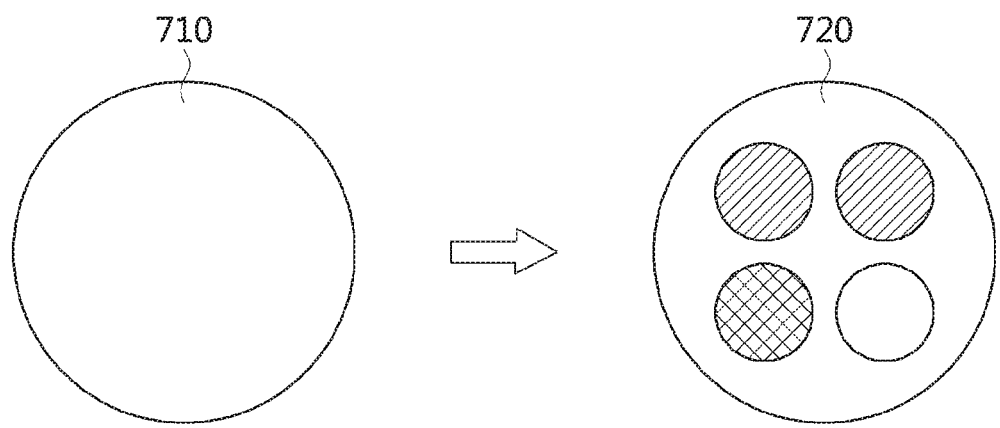
FIG. 7 is a view illustrating a change in a magnetic field according to an embodiment of the present invention.

FIG. 7 is a view illustrating a change in a magnetic field according to an embodiment of the present invention.

Referring to FIG. 7, a single solenoid coil or each of two solenoid coils according to an embodiment of the present invention may generate a magnetic field having a uniform strength.

Here, when magnetic nanoparticle samples are mounted in a single solenoid coil or two solenoid coils according to the embodiment of the present invention, the strength of a magnetic field in a portion in which each magnetic nanoparticle sample is mounted may be modified.

For example, it may be assumed that an area corresponding to the left circle illustrated in FIG. 7 is a before-modification magnetic field 710 indicating a magnetic field existing before the magnetic field is modified. In this case, when magnetic nanoparticle samples are mounted in a single solenoid coil or two solenoid coils, the strength of the magnetic field is partially and differently modified, as illustrated in the right circle in FIG. 7, after which a magnetic field 720 may be generated.

Therefore, since the present invention does not use a large number of coils as in the case of the conventional technology, the use of equipment, such as a power supply or current control equipment that is difficult to handle and is dangerous, may be minimized.

Further, in general, the coil used in the conventional technology is very difficult to manufacture and is expensive. In contrast, the magnetic field modification system using magnetic nanoparticles as in the case of the present invention may be more easily implemented by adjusting the capacity or concentration of magnetic nanoparticles in a container that holds the magnetic nanoparticles.

Furthermore, when an electromagnetic field is induced in a specific space using multiple coils, a system function corresponding thereto must be separately developed, but when magnetic nanoparticles are used, a magnetic field having a desired strength may be very easily formed in a desired space.

Figure 8:
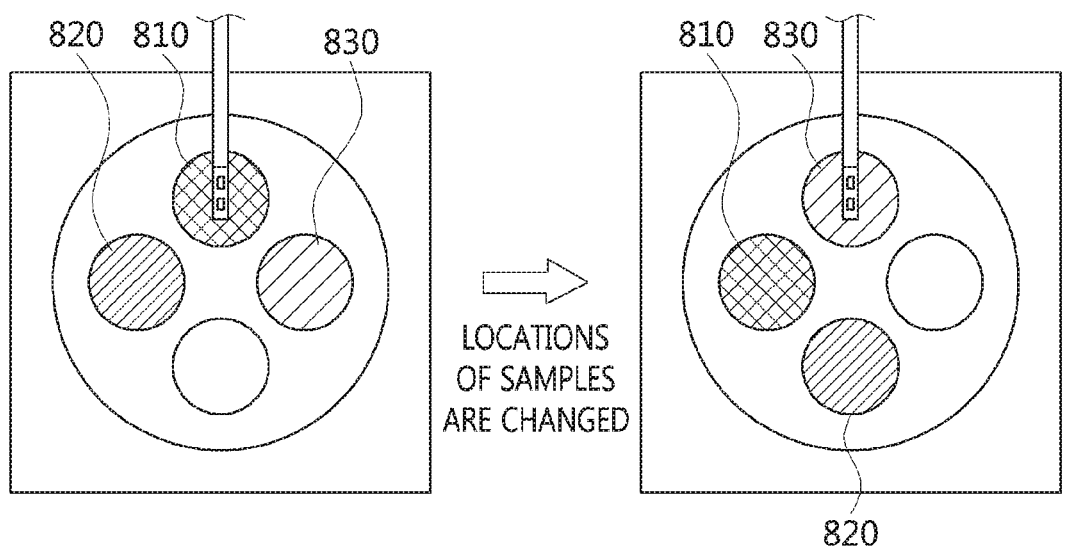
FIG. 8 is a view illustrating an example in which the locations of magnetic nanoparticle samples are changed by rotating an acrylic structure according to the present invention.

FIG. 8 is a view illustrating an example in which the locations of magnetic nanoparticle samples are changed by rotating an acrylic structure according to the present invention.

Referring to FIG. 8, the acrylic structure according to the present invention may be detachably provided in the cylinder of a solenoid coil. For example, a suitable acrylic structure may be used in consideration of the shapes of samples to be muffled in the acrylic structure and the shapes of sample-mounting holes formed in the acrylic structure.

Here, magnetic nanoparticle samples according to the embodiment of the present invention may be used by putting a solution containing magnetic nanoparticles in a plastic container, and data about the changed strength of a magnetic field may be acquired using magnetic nanoparticle samples having various concentrations.

For example, it may be assumed that a magnetic nanoparticle sample 810 illustrated in FIG. 8 is an undiluted solution having a concentration of 100%, a magnetic nanoparticle sample 820 has a concentration of 50%, and a magnetic nanoparticle sample 830 has a concentration of 25%. In this case, in order to more precisely measure changes in the strength of a magnetic field using respective samples, there is a need to mount the sample desired to be used at the location of the measurement sensor. In this case, the acrylic structure according the embodiment of the present invention may be rotated with the multiple magnetic nanoparticle samples 810, 820, and 830 mounted therein, and thus the locations of the multiple magnetic nanoparticle samples 810, 820, and 830 may be changed.

For example, assuming that the strength of a magnetic field is 30 Gauss when the magnetic nanoparticle sample 810, which is the undiluted solution, is located at the measurement sensor, the strength of the magnetic field may be measured as 26 Gauss when the magnetic nanoparticle sample 820 is located at the measurement sensor, and may be measured as 22 Gauss when the magnetic nanoparticle sample 830 is located at the measurement sensor.

Figure 9:
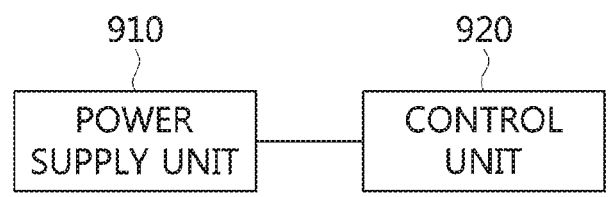
FIG. 9 is a block diagram illustrating an apparatus for modifying a magnetic field according to an embedment of the present invention.

FIG. 9 is a block diagram illustrating an apparatus for modifying a magnetic field according to an embodiment of the present invention.

Referring to FIG. 9, the magnetic field modification apparatus according to the embodiment of the present invention includes a power supply unit 910 and a control unit 920.

The power supply unit 910 applies current o a single solenoid coil or two parallel solenoid coils.

The single solenoid coil or each of the two solenoid coils may be a coil in which a conducting wire made of copper or aluminum is spirally and uniformly wound and formed in a cylindrical shape. Therefore, when current is applied to the conducting wire, a magnetic field having a relatively uniform strength may be formed in the direction penetrating into the cylindrical shape.

Here, the two solenoid coils may have a shape corresponding to any one of a Helmholtz coil and a Maxwell coil.

The Helmholtz coil may be composed of two identical solenoid coils, and may be configured such that the two solenoid coils are arranged parallel to each other while sharing a central axis with each other, with an area for magnetic field measurement being interposed therebetween.

The Maxwell coil has evolved from the Helmholtz coil and generates a magnetic field that is much more uniform than that of the Helmholtz coil, but requires more complicated settings than that of the Helmholtz coil.

Here, the current may be supplied through a power supply.

When a preset target location is in a 2D space, current may be applied to the single solenoid coil, and when the preset target location is in a 3D space, current may be applied to the two solenoid coils. That is, when a user desires to generate a magnetic field having a desired strength in a 2D space, the magnetic field may be generated by applying current only to one solenoid coil, and when the user desires to generate a magnetic field having a desired strength in a 3D space, the magnetic field may be generated by applying current to the two solenoid coils.

Since the structure for generating a magnetic field in a 2D space and a structure for generating a magnetic field in a 3D space has been described in detail with reference to FIGS. 2 and 3, a detailed description thereof will be omitted here.

The control unit 920 measures the strength of a magnetic field generated by the current at the preset target location using a measurement sensor.

Here, the target location may be the location where the strength of the magnetic field is to be subsequently modified through a magnetic nanoparticle sample. Therefore, at the target location, a sample-mounting hole in which the magnetic nanoparticle sample is to be mounted may be present.

Therefore, the strength of the magnetic field may be measured based on the central point of the sample-mounting hole in which the magnetic nanoparticle sample is not yet mounted.

The sample-mounting hole is included in the acrylic structure to fix the magnetic nanoparticle sample, and the structure of the sample-mounting hole has been described in detail with reference to FIG. 4, and thus a detailed description thereof will be omitted here.

Here, the measurement sensor may measure the strength of a magnetic field while moving on an X axis and a Y axis in the area of an internal concentric circle in which the magnetic field is generated through the solenoid coil. Therefore, the measurement sensor may be moved while being fixed on an XY stage, on which the measurement sensor can be moved on the X axis and the Y axis.

Since the detailed structures of the measurement sensor and the XY stage have been described in detail with reference to FIGS. 2 and 3, a detailed description thereof will be omitted here.

Further, the control unit 920 controls the strength of the magnetic field based on the concentration of the magnetic nanoparticle sample mounted in the single solenoid coil or two solenoid coils so that the strength of the magnetic field matches the preset target value.

For example, when magnetic nanoparticles are present at the location at which the magnetic field is formed, a change in the magnetic field may occur due to the magnetic force of the magnetic nanoparticles. Therefore, the strength of the magnetic field may be controlled by adjusting such a change using the concentration of the magnetic nanoparticles.

The magnetic nanoparticle sample may be mounted in a cylinder corresponding to the single solenoid coil or two solenoid coils.

For example, a container filled with a solution containing the magnetic nanoparticles may be fitted into the sample-mounting hole, and may then be mounted in the cylinder corresponding to the solenoid coil.

Here, multiple magnetic nanoparticle samples may be used, and may have different concentrations of magnetic nanoparticles.

For example, a first sample, in which the concentration of magnetic nanoparticles is 100%, a second sample, in which the concentration of magnetic nanoparticles is 50%, and a third sample, in which the concentration of magnetic nanoparticles is 25%, may be simultaneously mounted in a single solenoid coil.

Since the method for mounting a magnetic nanoparticle sample in the sample-mounting hole has been described in detail with reference to FIGS. 5 and 6, a detailed description thereof will be omitted here.

When magnetic nanoparticle samples are intended to be mounted in two solenoid coils, the magnetic nanoparticle samples may be mounted in one or more of the two solenoid coils. That is, the magnetic nanoparticle samples may be mounted in only one of the two solenoid coils or may be mounted in the two solenoid coils, thus modifying a magnetic field.

By means of this magnetic field modification apparatus, the modification of a magnetic field may be partially induced in a solenoid coil-type electromagnetic field generation device.

Also, there can be provided a magnetic field modification apparatus, which can minimize the use of equipment required for the modification of the strength of a magnetic field and which can be more easily used and can be more efficiently implemented from the standpoint of expense than other methods using multiple coils.

Figure 10:
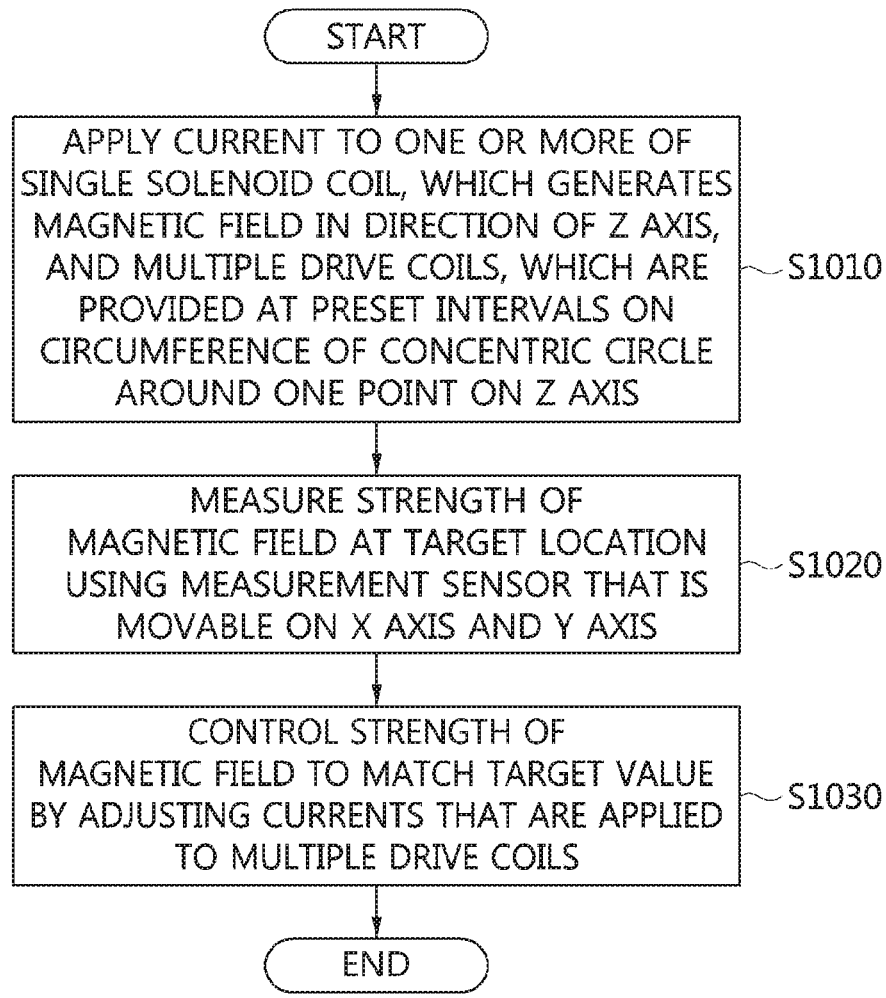
FIG. 10 is an operation flowchart illustrating a method for controlling a magnetic field according to an embodiment of the present invention.

FIG. 10 is an operation flowchart illustrating a method for controlling a magnetic field according to an embodiment of the present invention.

Referring to FIG. 10, in the magnetic field control method according to the embodiment of the present invention, current is applied to one or more of a single solenoid coil, which generates a magnetic field in the direction of a Z axis, and multiple drive coils, which are provided at preset intervals on the circumference of a concentric circle around one point on the Z axis, at step S1010.

Here, the Z axis may correspond to the direction penetrating into the cylinder of the single solenoid coil.

For example, the single solenoid coil may be a coil in which a conducting wire made of copper or aluminum is spirally and uniformly wound and formed in a cylindrical shape. Therefore, when current is applied to the conducting wire, a magnetic field having a relatively uniform strength may be formed in the direction penetrating into the cylindrical shape.

Here, the multiple drive coils may also have the shapes of solenoid coils, and may be provided such that the Z axes corresponding to respective drive coils face the Z axis of the single solenoid coil. Therefore, when currents are applied to respective drive coils, multiple magnetic fields may be formed.

The single solenoid coil and the concentric circle may be located parallel to each other. That is, when viewed from the side of the single solenoid coil, the single solenoid coil and the multiple drive coils may be located parallel to each other without overlapping each other.

The multiple drive coils may be fixed while being attached to a separate circular structure. Detailed structures of the single solenoid coil and multiple drive coils will be described in detail later with reference to FIGS. 13 and 14.

Individual currents may be applied to the multiple drive coils using a relay and a variable resistor.

The relay may distribute current, supplied from a power supply, in accordance with the number of multiple drive coils. Also, a number of variable resistors corresponding to the number of drive coils may be provided and used to control the magnitudes of the individual currents distributed through the relay.

For example, when the current is supplied to the relay through at least one power supply, the relay may distribute the current so that distributed currents can be individually applied to respective drive coils. Thereafter, the individual currents distributed by the relay may be applied to respective drive coils through the multiple variable resistors.

Here, the structure for applying currents will be described in detail later with reference to FIG. 12.

The individual currents may be simultaneously applied to respective drive coils, or alternatively, an individual current may be separately applied to each of the drive coils.

Each individual current may be applied by controlling the relay based on Arduino board.

Next, in the magnetic field control method according to the present invention, the strength of a magnetic field is measured at a target location at which the magnetic field is to be generated, using a measurement sensor that is movable on an X axis and a Y axis, at step S1020.

The target location may be the location at which the user desires to generate a magnetic field.

The measurement sensor may measure the strength of the magnetic field while moving on the X axis and the Y axis within the single solenoid coil, that is, within the concentric circle in which multiple drive coils are provided. Therefore, the measurement sensor may be moved while being fixed on an XY stage on which the measurement sensor is movable on the X axis and the Y axis, and the XY stage may be connected to the Arduino board to control the location of the measurement sensor.

The detailed structures of the measurement sensor, the XY stage, and the Arduino board will be described in detail later with reference to FIG. 11.

Next, in the magnetic field control method according to the embodiment of the present invention, the strength of the magnetic field is controlled such that the strength of the magnetic field matches a preset target value by adjusting the currents that are applied to the multiple drive coils at step S1030.

For example, when the values of currents that are respectively applied to the multiple drive coils are changed, the strengths of magnetic fields formed through respective drive coils are also changed, and thus the value measured by the measurement sensor may also be changed. Therefore, the strengths of magnetic fields formed through multiple drive coils may be controlled based on current so that a magnetic field having the strength desired by the user is produced.

Here, individual currents may be adjusted by adjusting respective variable resistors for the multiple drive coils.

For example, the individual currents that are applied to the multiple drive coils may be adjusted in such a way that the values of the individual currents are decreased by increasing the resistance of the variable resistors or are increased by decreasing the resistance of the variable resistors.

Here, the strengths of the magnetic fields may be controlled by changing the locations of poles corresponding to the single solenoid coil. A detailed description thereof will be made later with reference to FIGS. 19 and 20.

Here, each drive coil is configured such that a magnetic plunger is located inside a solenoid coil, and has a structure in which, when current is applied to the solenoid coil, the magnetic plunger is moved to the inside of the solenoid coil and then generates a strong magnetic field. Here, the magnetic plunger may be made of a typical metal material which is not polar when current is not applied to the solenoid coil. However, when current is applied to the solenoid coil, the magnetic plunger exhibits magnetism while becoming a magnet through a magnetic field formed by the solenoid coil, thus forming a strong magnetic field.

Therefore, the magnetic field control method may perform control such that a magnetic field having a desired strength is generated at the location desired by the user using strong magnetic fields generated through multiple drive coils.

By means of this magnetic field control method, a Nuclear Magnetic Resonance (NMR) system or an Electron Paramagnetic Resonance Imaging (EPRI) system for acquiring an image using a fixed gradient field may generate an electromagnetic field in a specific space.

Also, technology for generating a magnetic field having the strength desired by the user at a desired location may be provided, and may then be applied to a system using electron resonance or nuclear resonance and, in addition, an image acquisition scheme that is active rather than passive, as in the case where a gradient field is used, may be provided.

Figure 11:
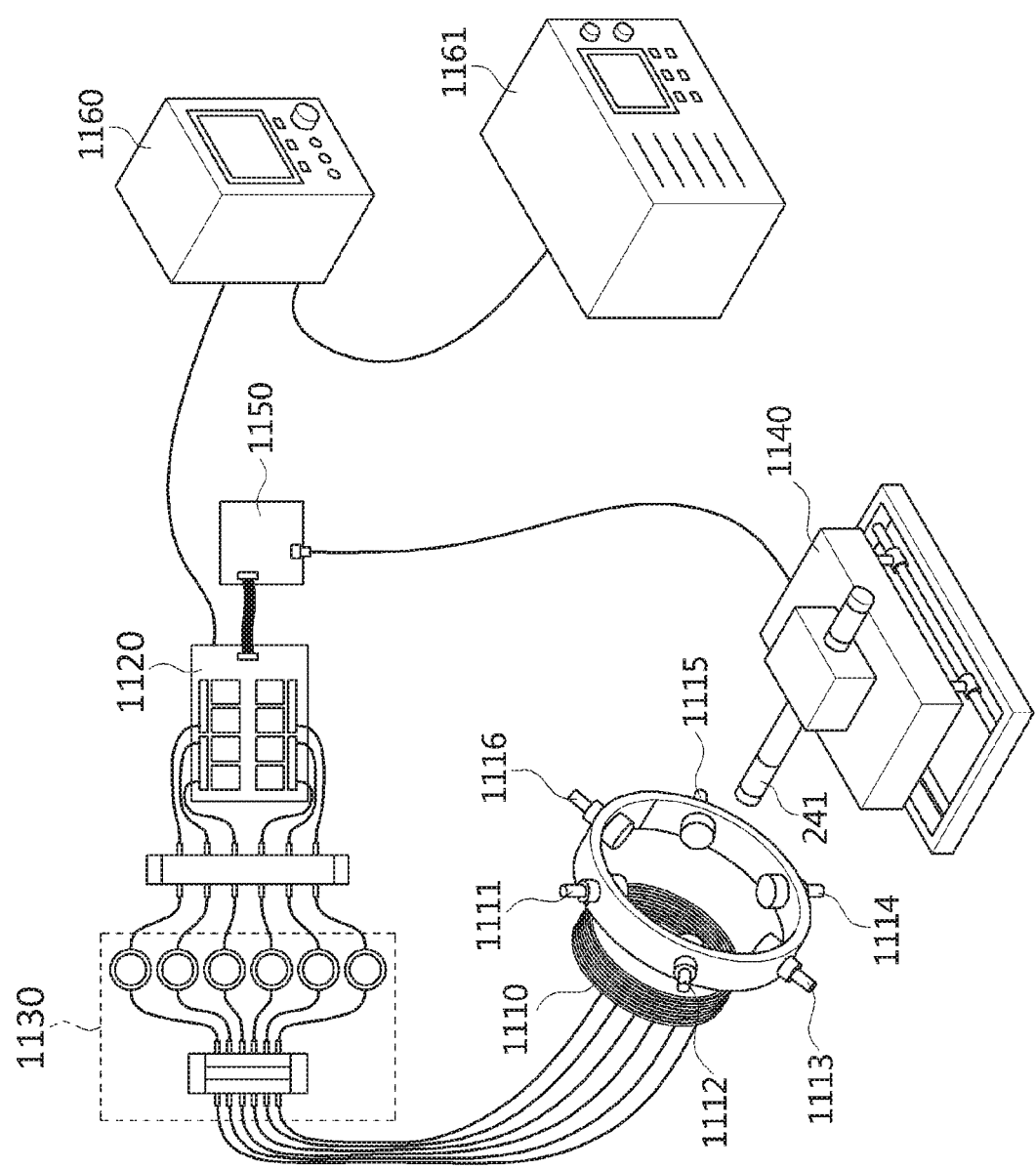
FIG. 11 is a view illustrating a magnetic field, control system according to an embedment of the present invention.

FIG. 11 is a view illustrating a magnetic field control system according to an embedment of the present invention.

Referring to FIG. 11, the magnetic field control system according to the embodiment of the present invention includes a single solenoid coil 1110, multiple drive coils 1111 to 1116, a relay 1120, a variable resistor 1130, an XY stage 1140, a measurement sensor 1141, an Arduino board 1150, and power supplies 1160 and 1161.

Hereinafter, a process for supplying power and measuring a magnetic field will be sequentially described.

First, the magnetic field control system according to the embodiment of the present invention may supply power or current to the relay 1120 through the one or more power supplies 1160 and 1161.

Here, the relay 1120 may distribute the supplied current in accordance with the number of drive coils 1111 to 1116 and apply the distributed currents to the multiple drive coils 1111 to 1116.

The relay 1120 may be controlled and operated based on the Arduino board 1150.

The variable resistor 1130 may be present between the relay 1120 and the multiple drive coils 1111 to 1116. The variable resistor 1130 may control individual currents distributed through the relay 1120.

Thereafter, when current is applied to one or more of the single solenoid coil 1110 and the multiple drive coils 1111 to 1116, a magnetic field may be formed in the single solenoid coil 1110 and the multiple drive coils 1111 to 1116.

Here, the XY stage 1140 may be operated to move the measurement sensor 1141 on an X axis and a Y axis, thus enabling the strength of the magnetic field to be measured at a specific location.

The XY stage 1140 may be controlled based on the Arduino board 1150 so as to move the measurement sensor 1141.

Thereafter, whether the strength of the magnetic field measured by the measurement sensor 1141 matches a preset target value may be determined. When the measured strength of the magnetic field does not match the preset target value, control may be performed such that the strength of the magnetic field matches the preset target value by adjusting the magnitudes of individual currents that are applied to the multiple drive coils 1111 to 1116.

Here, the magnitudes of individual currents that are applied to the multiple drive coils 1111 to 1116 may be adjusted by controlling the relay 1120 or the variable resistor 1130 based on the Arduino board 1150.

Figure 12:
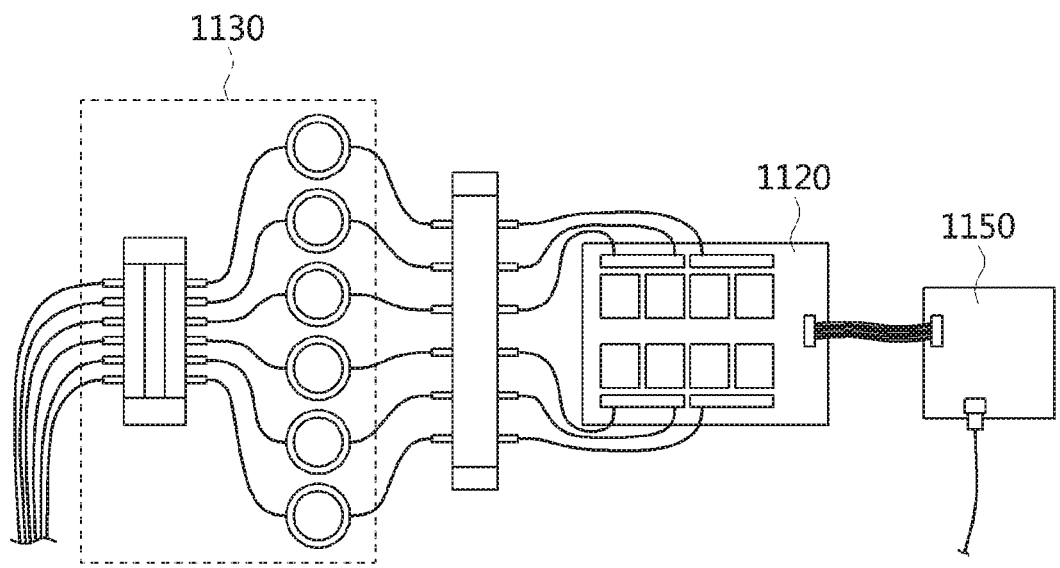
FIG. 12 is a view illustrating a current control system in the magnetic field control system of FIG. 11.

FIG. 12 is a view illustrating an example of the current control system of the magnetic field control system illustrated in FIG. 11.

Referring to FIG. 12, the current control system of the magnetic field control system illustrated in FIG. 11 includes the relay 1120, the variable resistor 1130, and the Arduino board 1150.

The Arduino board 1150 may be a device having a basic device that is capable of executing and processing commands, and may enable sensors or parts to be freely connected thereto and to apply the user's settings through a computer.

Therefore, in order to apply individual currents to multiple drive coils depending on the user's settings, the relay 1120 connected through the Arduino board 1150 may be controlled.

Here, the relay 1120 may distribute current based on values controlled by the Arduino board 1150. For example, the current supplied through a power supply may be distributed in accordance with the number of multiple drive coils.

Thereafter, the magnitudes of individual distributed currents may be adjusted through the variable resistor 1130.

Here, the value of the variable resistor 1130 may also be adjusted depending on the user's settings.

Figure 13:
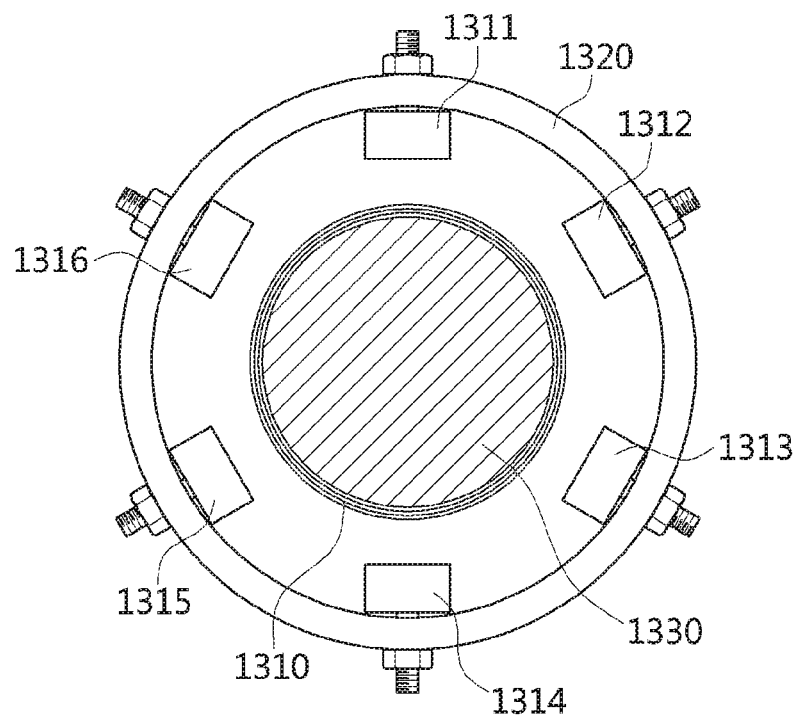
FIG. 13 is a front view illustrating multiple coils according to an embodiment of the present invention.
Figure 14:
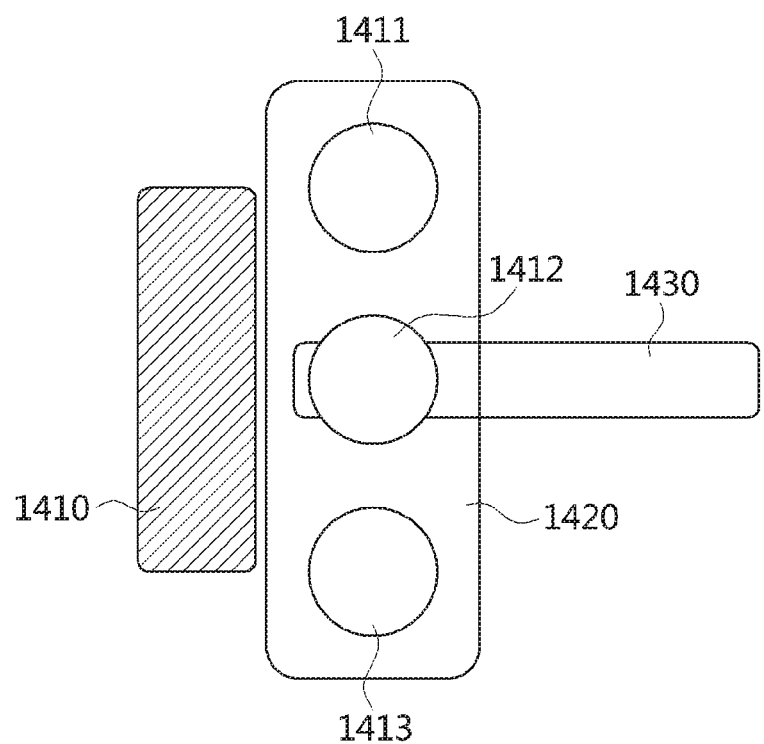
FIG. 14 is a side view illustrating multiple coils and a measurement sensor according to an embodiment of the present invention.

FIG. 13 is a front view illustrating multiple coils according to an embodiment of the present invention, and FIG. 14 is a side view illustrating multiple coils and a measurement sensor according to an embodiment of the present invention.

Referring to FIGS. 13 and 14, the multiple coils according to the embodiment of the present invention may be provided in a form in which multiple drive coils 1311 to 1316 are located around a single solenoid coil 1310.

Here, the single solenoid coil 1310 and the multiple drive coils 1311 to 1316 may be located parallel to each other without overlapping each other, as illustrated in FIG. 13.

Also, the multiple drive coils 1311 to 1316 may be fastened to a separate acrylic structure 1320 in order to be fixed at their locations. Here, the acrylic structure 1320 may be installed such that the central point thereof is located on a Z axis penetrating into the single solenoid coil 1310. That is, both the central point of a concentric circle generated by the single solenoid coil 1310 and the central point of a concentric circle generated by the acrylic structure 1320 may be located on the Z axis.

Here, the single solenoid coil 1310 may generate a magnetic field in the direction of the Z axis, and each of the multiple drive coils 1311 to 1316 may generate a magnetic field in a direction facing the Z axis of the single solenoid coil 1310.

The measurement sensor according to the embodiment of the present invention may measure the strength of the magnetic field while moving on an X axis and a Y axis in an area 1330 illustrated in FIG. 13.

For example, as illustrated in FIG. 14, a measurement sensor 1430 connected to the XY stage may measure the strength of a magnetic field in an area in which a magnetic field generated by a single solenoid coil 1410 is mixed with magnetic fields generated by multiple drive coils 1411 to 1413. For example, the strength of the magnetic field may be measured while the measurement sensor 1430 is freely moved in the area 1330 of FIG. 13.

After the measurement sensor 1430 is initialized (calibrated) to a zero point before being used, it may be used.

Here, FIG. 14 illustrates the multiple coils viewed from the side thereof, wherein overlapping drive coils may not be indicated in the drawing.

Figure 15:
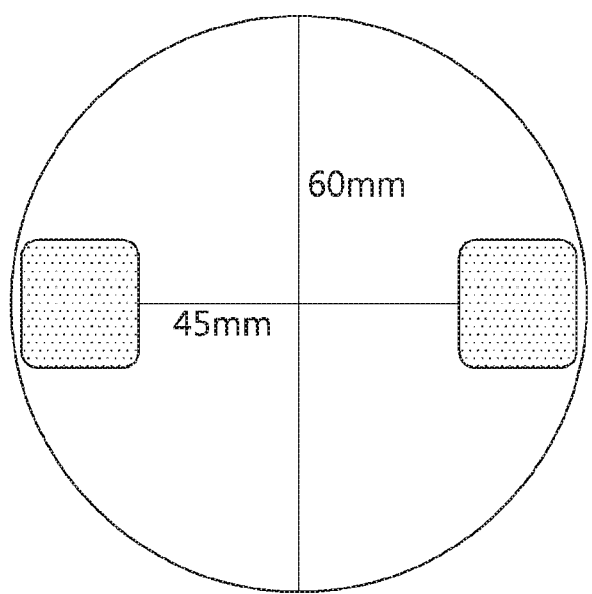
FIG. 15 is a sectional view illustrating the section of a drive coil according to an embodiment of the present invention.

FIG. 15 is a sectional view illustrating the section of a drive coil according to an embodiment of the present invention.

Referring to FIG. 15, the overall diameter of the drive coil according to the embodiment of the present invention may be 6 cm (i.e. 60 mm), and the internal diameter of the drive coil may be 4.5 cm (i.e. 45 mm), excluding the thickness of the coil. Therefore, the diameter of a magnetic plunger located in the drive coil may be less than 4.5 cm.

Figure 16:
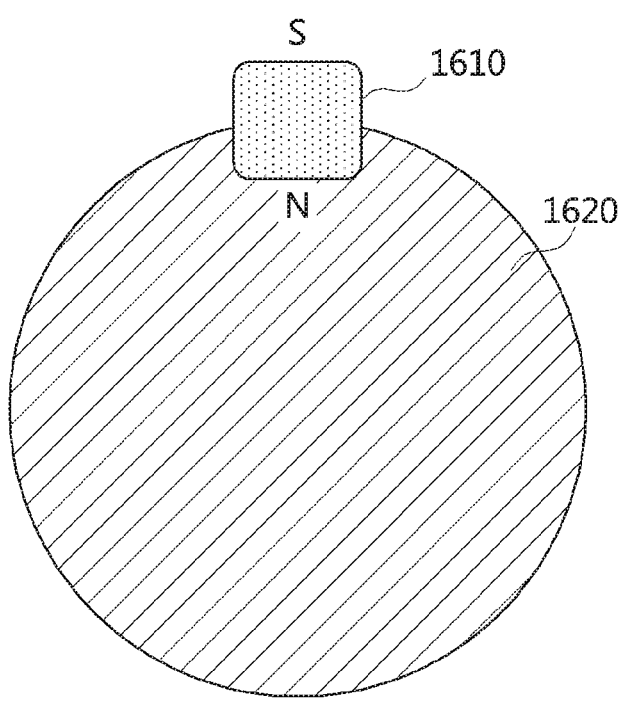
FIG. 16 is a view illustrating the polarities of a drive coil according to an embodiment of the present invention.

FIG. 16 is a view illustrating the polarities of a drive coil according to an embodiment of the present invention, and FIGS. 17 to 20 are views illustrating a change in magnetic field strength measured by a measurement sensor through current control according to an embodiment of the present invention.

Referring to FIGS. 16 to 20, the largest circle illustrated in FIGS. 17 to 20 may be the entire surface of an acrylic structure to which drive coils 1 to 6 are fixed, and small circles present in the largest circle may be respective measurement locations 1701 to 1707 at which the strength of a magnetic field is measured by a measurement sensor.

Here, numerals indicated in the measurement locations 1701 to 1707 denote measured magnetic field strengths, and a measurement unit may be millitesla (mT).

Further, the single solenoid coil according to the embodiment of the present invention is characterized in that a pole facing the measurement sensor may be changed depending on the direction in which the coil is wound. Further, as illustrated in FIG. 16, the multiple drive coils are characterized in that a side facing the inside 1620 of a concentric circle provided with the corresponding drive coil 1610 is an N pole.

The embodiments illustrated in FIGS. 17 to 20 show the strength of a magnetic field measured using a Kanetec Tesla Meter (TM 701) as the measurement sensor.

Figure 17:
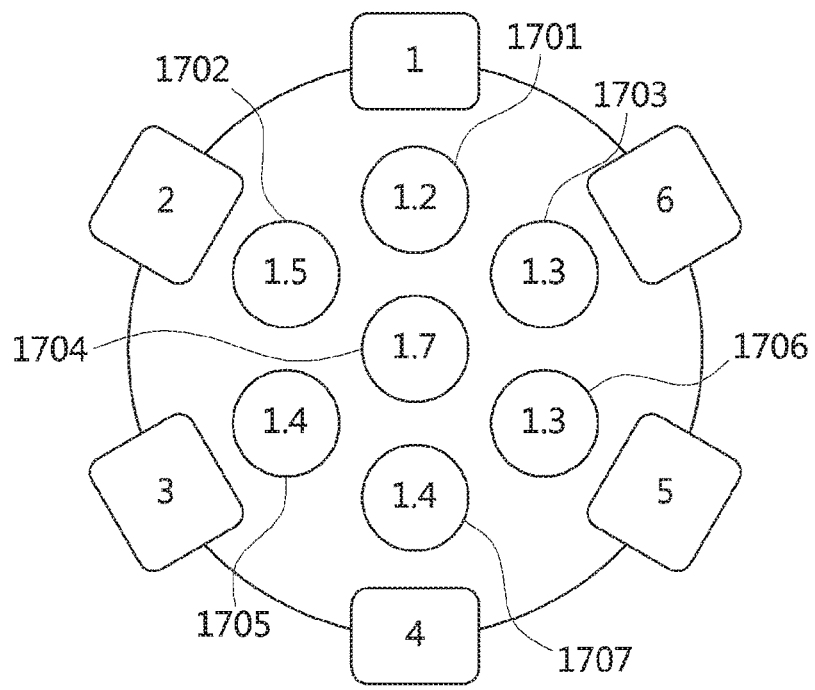
FIGS. 17 to 20 are views illustrating a change in magnetic field strength measured by a measurement sensor through current control according to an embodiment of the present invention.
Figure 18:
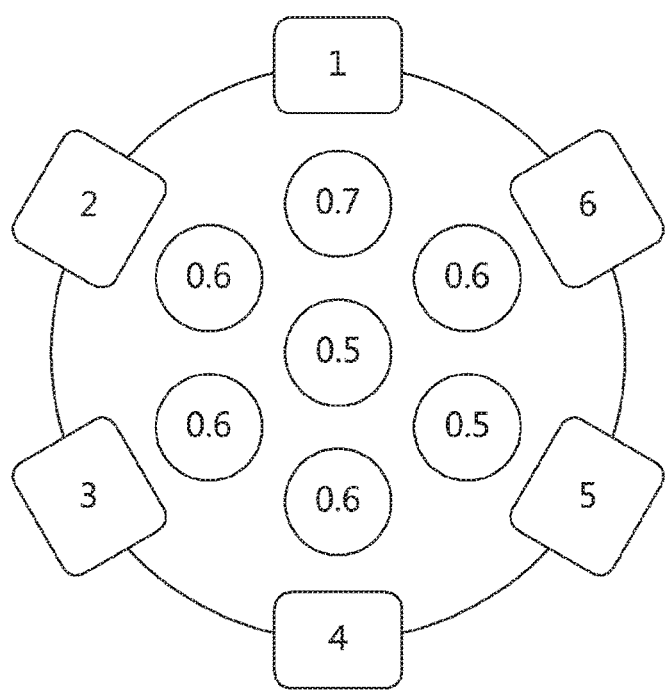

First, the embodiment of FIG. 17 shows the strengths of magnetic fields measured when a voltage of 1 V and a current of 0.66 A are applied only to the single solenoid coil, and the embodiment of FIG. 18 shows the strengths of magnetic fields measured when a voltage of 7 V and a current of 0.28 A are applied to each of multiple drive coils.

That is, a magnetic field may be formed even if current is applied only to the single solenoid coil or is applied only to the drive coils.

Figure 19:
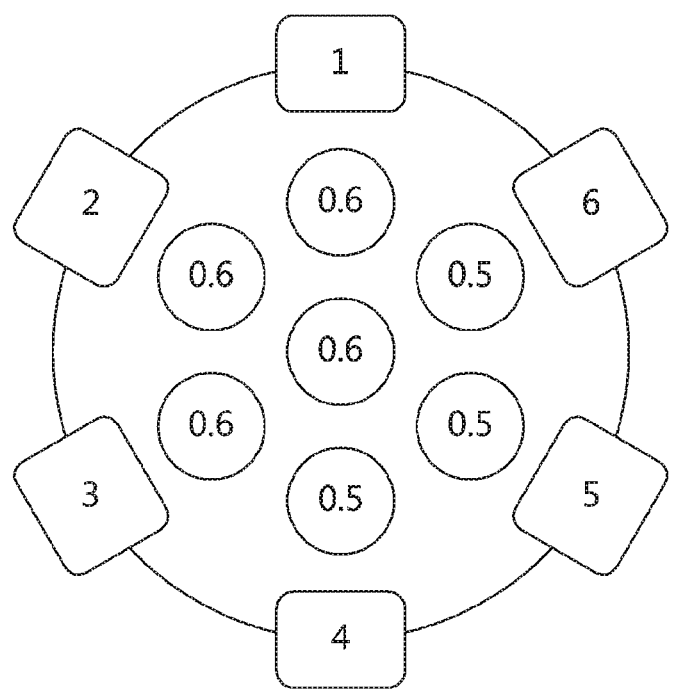
Figure 20:
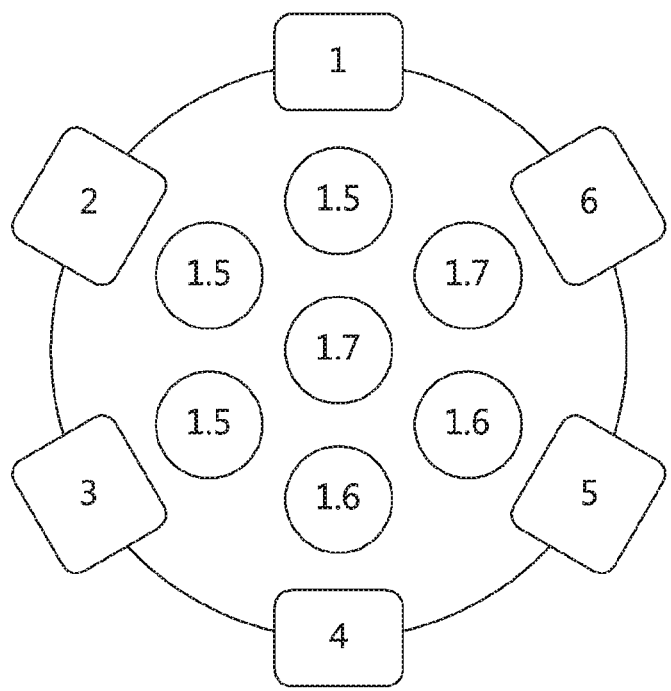

Further, the embodiments illustrated in FIGS. 19 and 20 show the strengths of magnetic fields measured when a voltage of 1 V and a current of 0.66 A are applied to a single solenoid coil and when a voltage of 7 V and a current of 0.28 A are applied to each of multiple drive coils. However, FIG. 19 shows that the S pole of the magnetic field generated by the single solenoid coil indicates the direction of the measurement sensor, and FIG. 20 shows that the N pole of the magnetic field generated by the single solenoid coil indicates the direction of the measurement sensor.

That is, FIG. 19 shows the results of measuring the strength of a magnetic field formed when the S pole of the magnetic field generated by the single solenoid coil meets the N poles of the magnetic fields generated by the multiple drive coils. Also, FIG. 20 shows the results of measuring the strength of a magnetic field formed when the N pole of the magnetic field generated by the single solenoid coil meets the N poles of the magnetic fields generated by the multiple drive coils.

Therefore, the strength of the magnetic field may be controlled using only the method of changing the location of the pole of the single solenoid coil.

Figure 21:
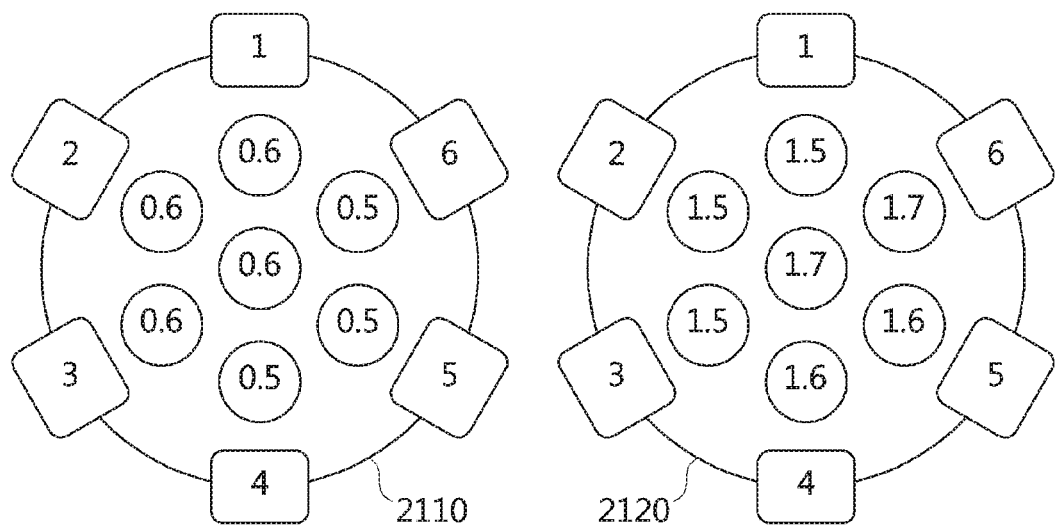
FIGS. 21 and 22 are diagrams illustrating examples in which the strength of a magnetic field is controlled using a variable resistor according to the present invention.
Figure 22:
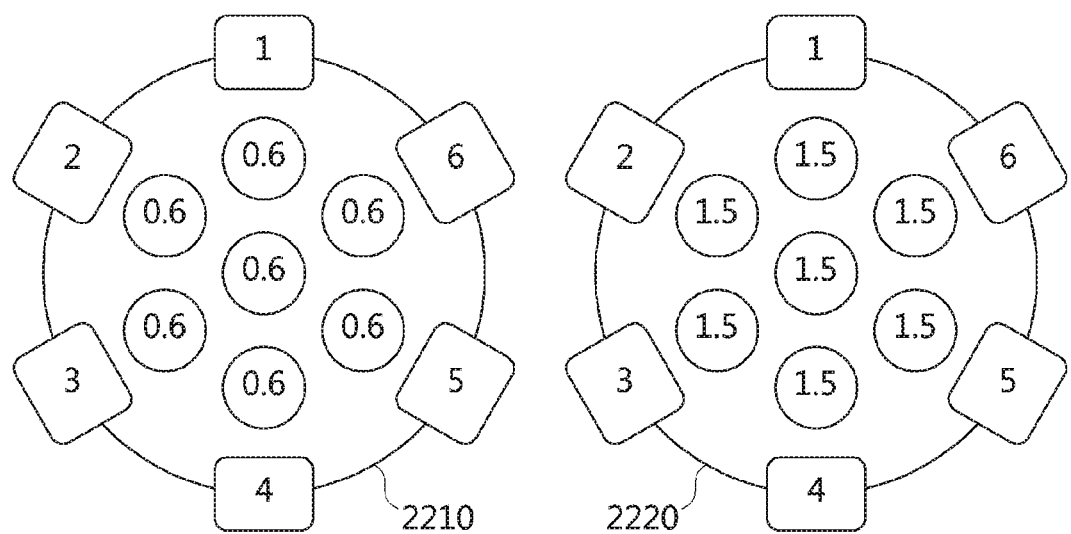

FIGS. 21 and 22 are diagrams illustrating examples in which the strength of a magnetic field is controlled using a variable resistor according to the present invention.

Referring to FIG. 21, a magnetic field measurement result 2110 may correspond to the strength of a magnetic field that is measured when a voltage of 1 V and a current of 0.66 A are applied to a single solenoid coil and when a voltage of 7 V and a current of 0.28 A are applied to each of multiple drive coils. Here, the magnetic field measurement result 2110 may be the result obtained when the S pole of the magnetic field generated by the single solenoid coil indicates the direction of the measurement sensor.

Also, a magnetic field measurement result 2120 may correspond to the strength of a magnetic field that is measured when a voltage of 1 V and a current of 0.66 A are applied to the single solenoid coil and when a voltage of 7 V and a current of 0.28 A are applied to each of multiple drive coils, but may indicate the strength of the magnetic field when the N pole of the magnetic field generated by the single solenoid coil indicates the direction of the measurement sensor.

Here, a result such as that of FIG. 22 may be acquired by finely adjusting the current that is applied to the multiple drive coils using the variable resistor according to the present invention.

That is, since the magnetic field measurement result 2110 of FIG. 21 shows that the strength of the magnetic field measured at some measurement locations is 0.5 mT, the magnetic field strength may be controlled such that all of measurement results are 0.6 mT, as shown in the magnetic field measurement result 2210 of FIG. 22, by adjusting the individual currents of some drive coils using the variable resistor.

Also, since the magnetic field measurement result 2120 of FIG. 21 shows that the measured magnetic field strengths are not uniform, namely being 1.5 mT, 1.6 mT, and 1.7 mT, the magnetic field strength may be controlled such that all of measurement results are 1.5 mT, as shown in magnetic field measurement result 2220 of FIG. 22, by adjusting the individual currents of some drive coils using the variable resistor.

Figure 23:
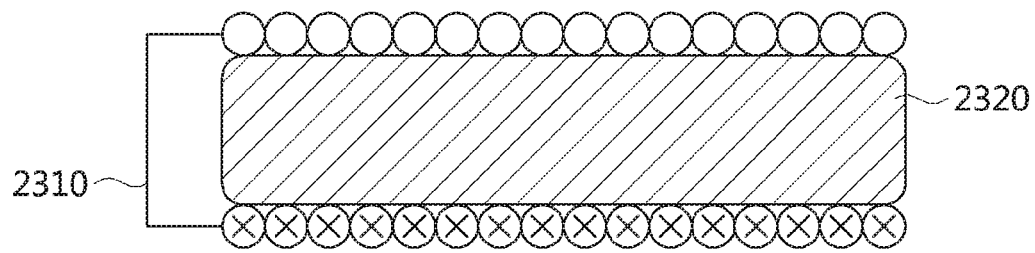
FIG. 23 is a view illustrating an example of a magnetic field generated in a gradient field scheme.
Figure 24:
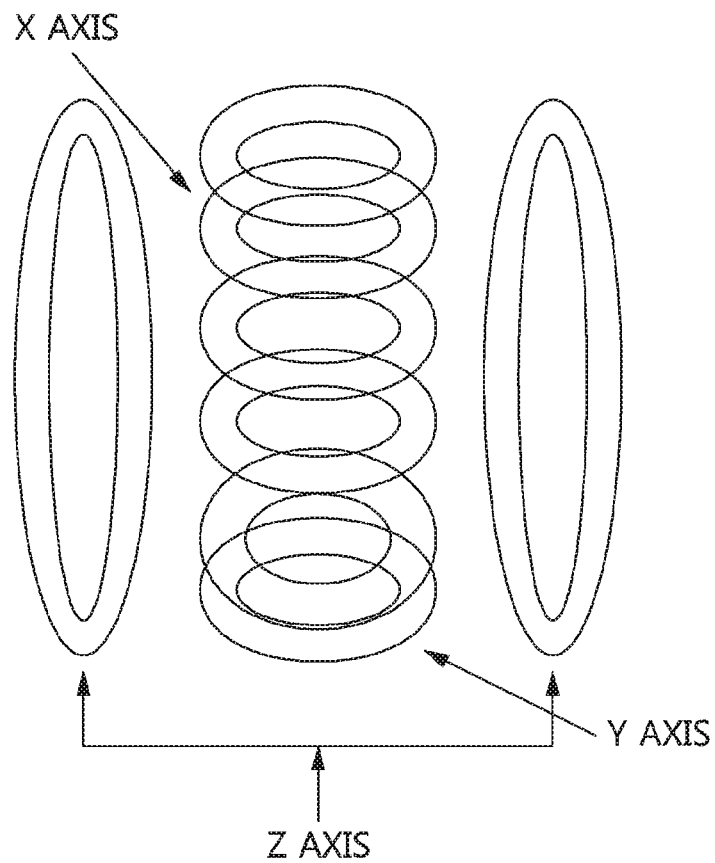
FIG. 24 is a view illustrating an example of a magnetic field generated according to the present invention.

FIG. 23 is a view illustrating an example of a magnetic field generated in a gradient field scheme, and FIG. 24 is a view illustrating an example of a magnetic field generated according to the present invention.

First, referring to FIG. 23, in existing medical imaging equipment, an image of the entire sample may be acquired using a fixed gradient field 2320. In order to acquire an image of a specific portion in the sample, a procedure for additionally applying a continuous RF field or pulse after the application of the fixed gradient field 2320 is required.

However, when the magnetic field control method according to the embodiment of the present invention is used, a magnetic field having a specific strength may be generated at a specific location by generating magnetic fields on an X axis and a Y axis, respectively, using the Z axis as a main axis, as illustrated in FIG. 24. This method may be applied even to a system that uses electron resonance or nuclear resonance, and may be effectively used for the acquisition of an image or information of a specific portion rather than the entire area of a sample.

Figure 25:
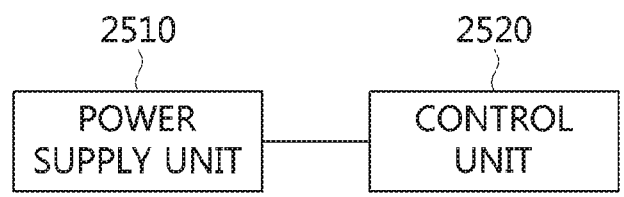
FIG. 25 is a block diagram illustrating an apparatus for controlling a magnetic field according to an embedment of the present invention.

FIG. 25 is a block diagram illustrating an apparatus for controlling a magnetic field according to an embodiment of the present invention.

Referring to FIG. 25, the magnetic field control apparatus according to the embodiment of the present invention includes a power supply unit 2510 and a control unit 2520.

The power supply unit 2510 applies current to one or more of a single solenoid coil, which generates a magnetic field in the direction of a Z axis, and multiple drive coils, which are provided at preset intervals on the circumference of a concentric circle around one point on the Z axis.

Here, the Z axis may correspond to the direction penetrating into the cylinder of the single solenoid coil.

For example, the single solenoid coil may be a coil in which a conducting wire made of copper or aluminum is spirally and uniformly wound and formed in a cylindrical shape. Therefore, when current is applied to the conducting wire, a magnetic field having a relatively uniform strength may be formed in the direction penetrating into the cylindrical shape.

Here, the multiple drive coils may also have the shapes of solenoid coils, and may be provided such that the Z axes corresponding to respective drive coils face the Z axis of the single solenoid coil. Therefore, when currents are applied to respective drive coils, multiple magnetic fields may be formed.

The single solenoid coil and the concentric circle may be located parallel to each other. That is, when viewed from the side of the single solenoid coil, the single solenoid coil and the multiple drive coils may be located parallel to each other without overlapping each other.

The multiple drive coils may be fixed while being attached to a separate circular structure. Since the detailed structures of the single solenoid coil and multiple drive coils have been described in detail with reference to FIGS. 13 and 14, a detailed description thereof will be omitted here.

Individual currents may be applied to the multiple drive coils using a relay and a variable resistor.

The relay may distribute current, supplied from a power supply, in accordance with the number of multiple drive coils. Also, a number of variable resistors corresponding to the number of drive coils may be provided and used to control the magnitudes of the individual currents distributed through the relay.

For example, when the current is supplied to the relay through at least one power supply, the relay may distribute the current so that distributed currents can be individually applied to respective drive coils. Thereafter, the individual currents distributed by the relay may be applied to respective drive coils through the multiple variable resistors.

Since the structure for applying currents has been described in detail with reference to FIG. 12, a detailed description thereof will be omitted here.

The individual currents may be simultaneously applied to respective drive coils, or alternatively, an individual current may be separately applied to each of the drive coils.

Each individual current may be applied by controlling the relay based on Arduino board.

The control unit 2520 measures the strength of a magnetic field at a target location at which the magnetic field is to be generated, using a measurement sensor that is movable on an X axis and a Y axis.

The target location may be the location at which the user desires to generate a magnetic field.

The measurement sensor may measure the strength of the magnetic field while moving on the X axis and the Y axis within the single solenoid coil, that is, within the concentric circle in which multiple drive coils are provided. Therefore, the measurement sensor may be moved while being fixed on an XY stage on which the measurement sensor is movable on the X axis and the Y axis, and the XY stage may be connected to the Arduino board to control the location of the measurement sensor.

Since the detailed structures of the measurement sensor, the XY stage, and the Arduino board have been described in detail with reference to FIG. 11, a detailed description thereof will be omitted here.

Furthermore, the control unit 2520 controls the strength of the magnetic field so that the strength of the magnetic field matches a preset target value by adjusting the currents that are applied to the multiple drive coils.

For example, when the values of currents that are respectively applied to the multiple drive coils are changed, the strengths of magnetic fields formed through respective drive coils are also changed, and thus the value measured by the measurement sensor may also be changed. Therefore, the strengths of magnetic fields formed through multiple drive coils may be controlled based on current so that a magnetic field having the strength desired by the user is produced.

Here, individual currents may be adjusted by adjusting respective variable resistors for the multiple drive coils.

For example, the individual currents that are applied to the multiple drive coils may be adjusted in such a way that the values of the individual currents are decreased by increasing the resistance of the variable resistors or are increased by decreasing the resistance of the variable resistors.

Here, the strengths of the magnetic fields may be controlled by changing the locations of poles corresponding to the single solenoid coil. Since this configuration has been described in detail with reference to FIGS. 19 and 20, a detailed description thereof will be omitted here.

Here, each drive coil is configured such that a magnetic plunger is located inside a solenoid coil, and has a structure in which, when current is applied to the solenoid coil, the magnetic plunger is moved to the inside of the solenoid coil and then generates a strong magnetic field. Here, the magnetic plunger may be made of a typical metal material which is not polar when current is not applied to the solenoid coil. However, when current is applied to the solenoid coil, the magnetic plunger exhibits magnetism while becoming a magnet through a magnetic field formed by the solenoid coil, thus forming a strong magnetic field.

Therefore, the magnetic field control apparatus may perform control such that a magnetic field having a desired strength is generated at the location desired by the user using strong magnetic fields generated through multiple drive coils.

In accordance with the present invention, the strength of a magnetic field may be modified using magnetic nanoparticles without using a multi-coil system.

Further, the present invention may minimize the use of equipment that is required in order to modify the strength of a magnetic field.

Furthermore, the present invention may provide a method for modifying a magnetic field, which is more easily used and is more efficiently implemented from the standpoint of expense than a method using multiple coils.

Furthermore, the present invention may provide a method that is capable of generating an electromagnetic field in a specific space in a Nuclear Magnetic Resonance (NMR) system or an Electron Paramagnetic Resonance Imaging (EPRI) system that acquires an image using a fixed gradient field.

Furthermore, the present invention may provide technology that is capable of generating a magnetic field having a strength desired by a user at a desired location, thus enabling the magnetic field to be applied to a system using electron resonance or nuclear resonance.

Furthermore, the present invention may selectively apply an electromagnetic field for producing resonance to a specific location in space.

In addition, the present invention may provide an image acquisition scheme that is active rather than being passive as in the case where a gradient field is used.

As described above, in the method for modifying and controlling a magnetic field and the apparatus therefor according to the present invention, the configurations and schemes in the above-described embodiments are not limitedly applied, and some or all of the above embodiments can be selectively combined and configured such that various modifications are possible.

What is claimed is:

1. A method for modifying a magnetic field, comprising:
    applying current to a single solenoid coil or to two parallel solenoid coils;
    measuring a strength of a magnetic field generated by the current at a preset target location using a measurement sensor; and
    controlling the strength of the magnetic field based on a concentration of one or multiple magnetic nanoparticle samples mounted in the single solenoid coil or the two solenoid coils so that the strength of the magnetic field matches a preset target value,
    wherein the one or more magnetic nanoparticle samples are detachably mounted in respective sample mounting holes of an acrylic structure provided in the solenoid coils.

2. The method of claim 1, wherein the one or more magnetic nanoparticle samples are mounted in a cylinder corresponding to the single solenoid coil or the two solenoid coils.

3. The method of claim 1, wherein controlling the strength of the magnetic field is performed using the one or more multiple magnetic nanoparticle samples, wherein the one or more magnetic nanoparticle samples have different concentrations of magnetic nanoparticles.

4. The method of claim 1, wherein applying the current is configured to, when the preset target location is in a two-dimensional (2D) space, apply the current to the single solenoid coil, and when the preset target location is in a three-dimensional (3D) space, apply the current to the two solenoid coils.

5. The method of claim 1, wherein the two solenoid coils have a shape corresponding to any one of a Helmholtz coil and a Maxwell coil.

6. The method of claim 2, wherein the one or more magnetic nanoparticle samples are mounted in one or more of the two solenoid coils when the magnetic nanoparticle sample is intended to be mounted in the two solenoid coils.

7. An apparatus for modifying a magnetic field, comprising:
    a power supply unit for applying current to a single solenoid coil or to two parallel solenoid coils; and
    a control unit for measuring a strength of a magnetic field generated by the current at a preset target location using a measurement sensor and controlling the strength of the magnetic field based on a concentration of one or more magnetic nanoparticle samples are mounted in the single solenoid coil or the two solenoid coils so that the strength of the magnetic field matches a preset target value,
    wherein the one or more magnetic nanoparticle samples are detachably mounted in respective sample mounting holes of an acrylic structure provided in the solenoid coils, and
    wherein the power supply unit is configured to, when the preset target location is in a two-dimensional (2D) space, apply the current to the single solenoid coil, and when the preset target location is in a three-dimensional (3D) space, apply the current to the two solenoid coils.

8. The apparatus of claim 7, wherein the one or more magnetic nanoparticle samples are mounted in a cylinder corresponding to the single solenoid coil or the two solenoid coils.

9. The apparatus of claim 7, wherein: the control unit is capable of using the one or more multiple magnetic nanoparticle samples, and the multiple magnetic nanoparticle samples have different concentrations of magnetic nanoparticles.

10. The apparatus of claim 7, wherein the two solenoid coils have a shape corresponding to any one of a Helmholtz coil and a Maxwell coil.

11. The apparatus of claim 8, wherein the one or more magnetic nanoparticle samples are mounted in one or more of the two solenoid coils when the magnetic nanoparticle sample is intended to be mounted in the two solenoid coils.

12. A method for controlling a magnetic field, comprising:
    applying current to one or more of a single solenoid coil for generating a magnetic field in a direction of a Z axis and multiple drive coils provided at preset intervals on a circumference of a concentric circle around one point on the Z axis;
    measuring a strength of a magnetic field at a target location at which the magnetic field is to be generated, using a measurement sensor that is movable on an X axis and a Y axis; and
    controlling the strength of the magnetic field by adjusting current to be applied to the multiple drive coils so that the strength of the magnetic field matches a preset target value.

13. The method of claim 12, wherein: applying the current is configured to apply individual currents to the multiple drive coils using a relay and variable resistors, and controlling the strength of the magnetic field is configured to adjust the individual currents by controlling respective variable resistors for the multiple drive coils.

14. The method of claim 12, wherein the single solenoid coil and the concentric circle are located parallel to each other.

* * * * *